(12) United States Patent
Rengifo et al.

(10) Patent No.: US 9,683,266 B2
(45) Date of Patent: Jun. 20, 2017

(54) GLUCOSE AND INSULIN SENSORS AND METHODS OF USE THEREOF

(75) Inventors: Raul Cuero Rengifo, Cypress, TX (US); Juliana Maria Navia, Bogota (CO)

(73) Assignee: INTERNATIONAL PARK OF CREATIVITY, Bogota (CO)

( * ) Notice: Subject to any disclaimer, the term of this patent is extended or adjusted under 35 U.S.C. 154(b) by 0 days.

(21) Appl. No.: 14/112,984

(22) PCT Filed: Apr. 19, 2012

(86) PCT No.: PCT/US2012/034170
§ 371 (c)(1),
(2), (4) Date: Jun. 9, 2014

(87) PCT Pub. No.: WO2012/145459
PCT Pub. Date: Oct. 26, 2012

(65) Prior Publication Data
US 2014/0287425 A1    Sep. 25, 2014

Related U.S. Application Data

(60) Provisional application No. 61/478,274, filed on Apr. 22, 2011.

(51) Int. Cl.
| | | |
|---|---|---|
| C12N 1/00 | (2006.01) |
| C12N 1/20 | (2006.01) |
| C12Q 1/68 | (2006.01) |
| G01N 33/66 | (2006.01) |
| G01N 33/74 | (2006.01) |

(52) U.S. Cl.
CPC .......... *C12Q 1/6897* (2013.01); *G01N 33/66* (2013.01); *G01N 33/74* (2013.01)

(58) Field of Classification Search
None
See application file for complete search history.

(56) References Cited

U.S. PATENT DOCUMENTS

| | | |
|---|---|---|
| 6,416,959 B1 | 7/2002 | Giuliano et al. |
| 6,537,806 B1 | 3/2003 | Osborne et al. |
| 2003/0148421 A1 | 8/2003 | Newgard et al. |
| 2004/0142356 A1 | 7/2004 | Patterson et al. |
| 2009/0137543 A1 | 5/2009 | Levine et al. |
| 2010/0021942 A1 | 1/2010 | Freemont et al. |
| 2010/0150871 A1 | 6/2010 | Thomas |
| 2010/0185047 A1 | 7/2010 | Khatib |
| 2011/0039327 A1 | 2/2011 | Wrinkler et al. |
| 2011/0071049 A1 | 3/2011 | Heintz |

FOREIGN PATENT DOCUMENTS

| | | |
|---|---|---|
| WO | 9640963 | 12/1996 |
| WO | 2005093075 | 10/2005 |
| WO | 2009037279 | 3/2009 |

OTHER PUBLICATIONS

Extended European Search Report for PCT/US2012/034170 dated Mar. 26, 2015, 11 pages.
Szabat et al., "Maturation of adult beta cells revealed using a Pdx1/insulan dual-reporter lentivirus," Endocrinology, 2009, 150:1627-1635.
Kim et al., "A dual-reporter system for specific tracing of pancreatic ss-cell lines that non-invasively measures viable in vivo islet cells," Biotechnology Letters, 2010, 32:53-57.
Ganzlin et al., "In-depth analysis of the Aspergillus niger glucoamylase (glaA) promoter performance using high-throughput screening and controlled bioreactor cultivation techniques," Journal of Biotechnology, 2008, 135:266-271.
Fukuzawa et al., "Development of a novel beta-cell specific promoter system for the identification of insulin-producing cells in in vitro cell cultures," Experimental Cell Research, 2006, 312:3404-3412.
Pedersen et al., "The promoter for the gene encoding the catalytic subunit of rat glucose-6-phosphatase contains two distinct glucose-responsive regions," American Journal of Physiology, Endocrinology and Metabolism, 2007, 292: E788-E801.
Ohtani et al., "Identification and characterization of a glucose-responsiveness region upstream of human insulin gene in transfected HIT-T 15 cells," Biopchemical and Biophysical Research Communications, 1998, 242:446-451.
Muzny et al. GenBank Accession AC094812; May 9, 2003 [online]; downloaded from http://www.ncbi.nlm.nih.gov/nuccore/AC094812 on Oct. 18, 2013, 53 pages.
Ullrich et al. GenBank Accession J00747; Apr. 27, 1883 [online]; downloaded from http://www.ncbi.nlm.nih.gov/nuccore/J00747, 3 pages.
Colicelli et al. GenBank Accession U33753 [online]. Sep. 19, 1995, downloaded from http://www.ncbi.nlm.nih.gov/nuccore/U33753 on Oct. 21, 2013, 3 pages.
Celenza et al. UniProt Accession P10870; Apr. 5, 2011 [online], downloaded from http://www.uniprot.org/uniprot/P10870 on Oct. 21, 2013, 4 pages.
McNally et al. UniProt Accession P00549; Apr. 5, 2011 [online], dowloaded from http://www.uniprot.org/uniprot/P00549 on Oct. 21, 2013, 6 pages.
Bernstein et al. UniProt Accession P07283; Apr. 5, 2011 [online], dowloaded from http://www.uniprot.org/uniprot/P07283 on Oct. 21, 2013, 4 pages.
Thompson et al. UniProt Accession P17505; Apr. 5, 2011 [online], downloaded from http://www.uniprot.org/uniprot/P17505 on Oct. 21, 2013, 4 pages.
Written Opinion for International Application No. PCT/US12/34170 dated Nov. 2, 2012, 10 pages.

*Primary Examiner* — Channing S Mahatan
(74) *Attorney, Agent, or Firm* — Gardner Groff Greenwald & Villanueva, PC

(57) ABSTRACT

Described herein are glucose and insulin sensors. The sensors are composed of host cells with DNA specifically designed to produce fluorescence when the cells come into contact with glucose and/or insulin in the sample. Once the fluorescence has been quantified, it can be correlated with the amount of glucose and/or insulin present in the sample.

10 Claims, 11 Drawing Sheets

GLUCOSE AND INSULIN SENSORS AND METHODS OF USE THEREOF

CROSS REFERENCE TO RELATED APPLICATIONS

This application claims priority upon U.S. provisional application Ser. No. 61/478,274, filed Apr. 22, 2011. This application is hereby incorporated by reference in its entirety for all of its teachings.

CROSS REFERENCE TO SEQUENCE LISTING

The DNA and RNA described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Diabetes is a degenerative disease, which is caused by abnormal levels of glucose in the cell. These abnormal levels of glucose are not easily predictable and or measurable. Currently, home use technologies to determine different levels of glucose are not very accurate or are not able to determine lower levels (below 20 mg/dl). Additionally, the abnormal levels of glucose have been correlated with the production of insulin. Type 1 diabetes is where the body is unable to produce insulin. Type 2 diabetes is when insulin is produced but the body destroys the insulin or is unable to recognize it.

Currently, the most used technologies to determine glucose levels involve enzyme reaction methods. These methods determine glucose in whole blood, plasma or serum. The methods include glucose oxidase, hexoquinase, and glucose dehydrogenase enzyme methods. The products of these reactions between the enzyme and blood sugar can be determined with colorimetric and spectrophotometric assays. Alternatively, they can be measured by the electric current produced in the reaction, which is the case for most commercially-available glucose meters. These methods are accurate and are becoming more sensitive, detecting glucose concentrations from 0 to 500 mg/dl for laboratory assays and 20 to 500 mg/dl for home monitoring. However, these methods can give falsely high values of glucose with different environmental or medical treatments. These methods can also provide uncertain values such as the incompatibility of the meters and the strips, which is one of the persistent problems of the methods.

The cost of current methods for measuring blood sugar levels is also an impediment, which ranges from about $0.35 to $1.00 for each strip used in home monitoring methods. Type 1 diabetics may test as often as 4 to 10 times a day. Thus, daily testing can be expensive. Manufacturers often provide meters at no cost to induce the use of the profitable test strips. For clinical laboratories, glucose determinations range from $3 to over $100 in the US and around the world. In the case of insulin analysis, prices range from $25 to $130 USD in the US and around the world. Diabetes diagnostic tests that include specific tests for measuring glucose and insulin levels can cost between $190 to $350, which is very expensive for diabetic patients.

The sensors and methods described herein address the issues of sensitivity and cost that are problems associated with current technologies available on the market.

SUMMARY

Described herein are glucose and insulin sensors. The sensors are composed of host cells such with DNA specifically designed to produce fluorescence when the cells come into contact with glucose and/or insulin in the sample. Once the fluorescence has been quantified, it can be correlated with the amount of glucose and/or insulin present in the sample. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
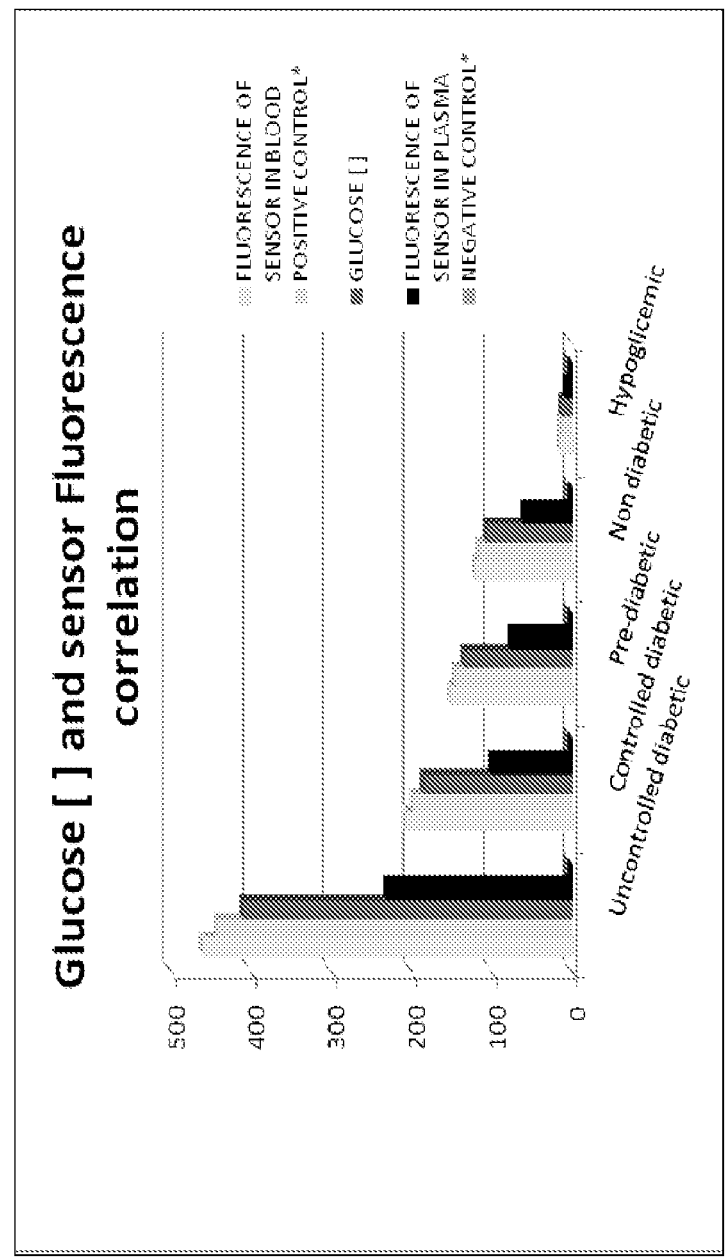
FIG. 1 shows (A) the equivalent proportion correlation of sensor fluorescence with clinical glucose values, demonstrating a direct relation for different patients including uncontrolled diabetic, controlled diabetic, pre-diabetic, non-diabetic and hypoglycemic patients; and (B) the equivalent proportion correlation of the DNA sensor and fluorescence when testing for glucose in different patients including uncontrolled diabetic, controlled diabetic, pre-diabetic, non diabetic and hypoglycemic patients.
Figure 1:
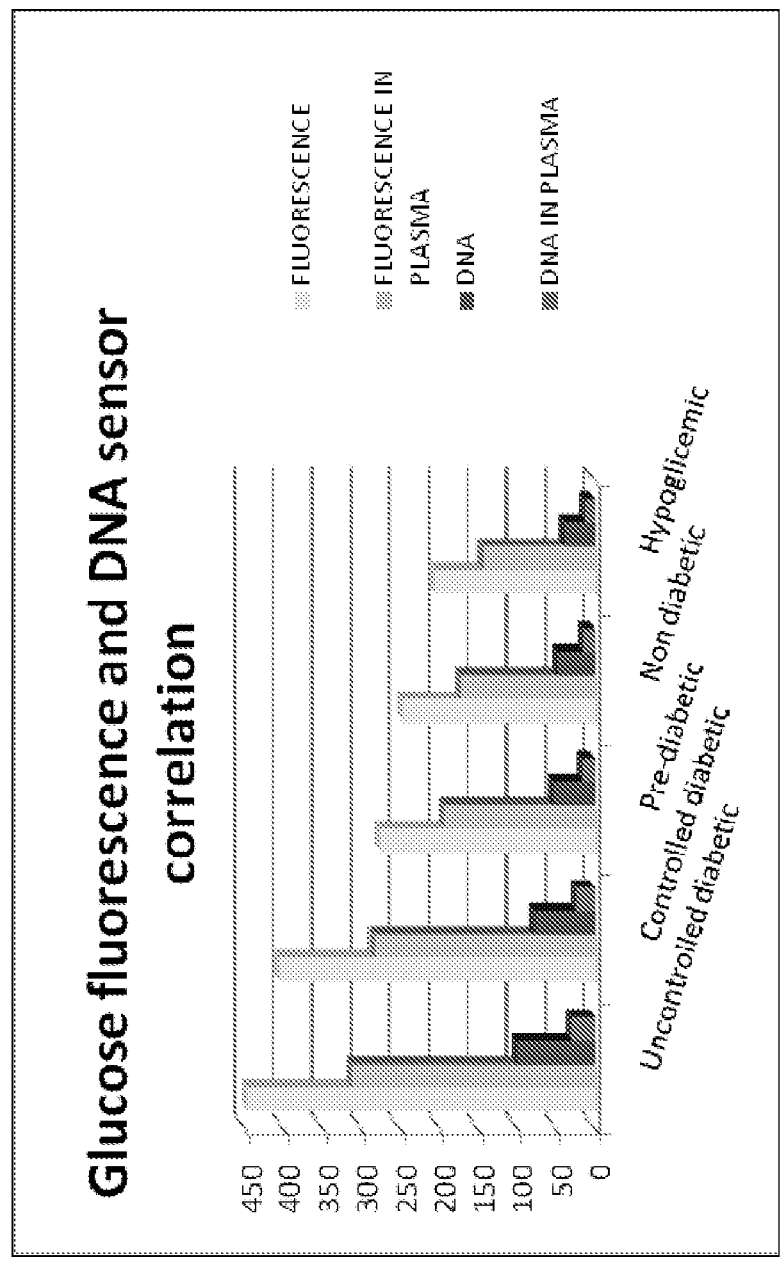

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Described herein are glucose and insulin sensors. The sensors are composed of host cells incorporated with DNA specifically designed to produce fluorescence when the cells come into contact with glucose and/or insulin in the sample. In one aspect, the sensor comprises a host cell comprising (1) a first DNA, wherein the first DNA comprises the following components in the following sequence: a glucose promoter, a glucose protein receptor, a ribosomal binding site, terminator, and a first reporter protein; (2) a second DNA, wherein the second DNA comprises the following components in the following sequence: an insulin promoter, a human insulin protein, a ribosomal binding site, a terminator, and a second reporter protein, or a combination thereof. In this aspect, the first DNA (referred to herein as "the glucose DNA") is specific to glucose, and the second DNA (referred to herein as "the insulin DNA") is specific to insulin. As will be discussed in detail below, the host cell can be transformed with both the glucose and insulin DNA in order to quantify the amount of glucose and insulin in the sample.

The host cells as referred to herein include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. The host cells can be naturally occurring cells or "recombinant" cells. Recombinant cells are distinguishable from naturally occurring cells in that they do not contain a recombinantly introduced nucleic acid. In one aspect, the host cell is a prokaryotic cell, such as, for example, *E. coli*. In other aspects, the host cell is yeast.

In order to effect expression of the glucose and insulin DNA, the DNA must be delivered into the host cell. This delivery may be accomplished in vitro, as in laboratory procedures for transforming cells lines using well developed procedures. Transformation of bacterial cell lines can be achieved using a variety of techniques. One method includes using calcium chloride. The exposure to the calcium ions renders the cells able to take up the DNA, or competent. Another method is electroporation. In this technique, a high-voltage electric field is applied briefly to cells, apparently producing transient holes in the cell membrane through which plasmid DNA enters. Exemplary procedures for transforming yeast with the glucose and insulin DNA are provided in the Examples. The glucose DNA and insulin DNA can be independently incorporated into the host cells (i.e., separate cell lines containing just glucose DNA and insulin DNA). Alternatively, the glucose DNA and insulin DNA can be incorporated into the same cells.

Once the glucose and/or insulin DNA has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. Furthermore, different media results in different growth rates and different stationary phase densities. A rich media results in a short doubling time and higher cell density at a stationary phase. Minimal media results in slow growth and low final cell densities. Efficient agitation and aeration increases final cell densities. A skilled artisan will be able to determine which type of media is best suited to culture a specific type of microorganism.

The glucose and insulin DNA referred to herein can be part of a vector that is incorporated into the host cells. In general, plasmid vectors containing replicon and control sequences that are derived from species compatible with the host cell are used in connection with these hosts. The vector ordinarily carries a replication site, as well as marking sequences that are capable of providing phenotypic selection in transformed cells. Plasmid vectors are well known and are commercially available. Such vectors include, but are not limited to, pWLNEO, pSV2CAT, pOG44, PXT1, pSG (Stratagene) pSVK3, pBSK, pBR322, pYES, PBSKII, and pUC vectors.

It is understood that one way to define the variants and derivatives of the glucose and insulin DNA herein is through defining the variants and derivatives in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed by published algorithms (see Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989, which are herein incorporated by reference for at least material related to nucleic acid alignment).

It is understood that the description of conservative mutations and homology can be combined together in any combination, such as embodiments that have at least 70%, 75%, 80%, 85%, 90%, 95%, or 99% homology to a particular sequence wherein the variants are conservative mutations. It is understood that any of the sequences described herein can be a variant or derivative having the homology values listed above.

The glucose DNA comprises the following components in the following sequence: a glucose promoter, a glucose protein receptor, a ribosomal binding site, terminator, and a first reporter protein. In certain aspects, the glucose DNA further comprises a ribosomal switch between the glucose protein receptor and the ribosomal binding site that can enhance translation and protein expression.

In one aspect, the glucose promoter in the glucose DNA is an ADH1 glucose promoter having SEQ ID NO. 1 or a derivative or variant thereof. In another aspect, the glucose promoter is SEQ ID NOS. 30-32 or a derivative or variant thereof.

In another aspect, the glucose protein receptor in the glucose DNA comprises a snf3 glucose protein receptor having SEQ ID NO. 2 or a derivative or variant thereof. In another aspect, the glucose protein receptor is SEQ ID NOS. 20-29 or a derivative or variant thereof.

In a further aspect, the ribosomal binding site in the glucose DNA comprises SEQ ID NOS. 4, 35, 36, or a derivative or variant thereof.

In another aspect, the terminator in the glucose DNA comprises SEQ ID NO. 5 or a derivative or variant thereof.

In certain aspects, when the glucose DNA further includes a ribosomal switch, the switch comprises SEQ ID NOS. 4, 34, 35, or a derivative or variant thereof.

In another aspect, the glucose DNA comprises the following components in the following sequence: an ADH1 glucose promoter having SEQ ID NO. 1, a snf3 glucose protein receptor having SEQ ID NO. 2, a ribosomal switch having SEQ ID NO. 3, a ribosomal binding site having SEQ ID NO. 4, a terminator having SEQ ID NO. 5, and a reporter protein.

The insulin DNA comprises the following components in the following sequence: an insulin promoter, a human insulin protein, a ribosomal binding site, a terminator, and a reporter protein. In certain aspects, the insulin DNA further comprises a ribosomal switch between the human insulin protein and the ribosomal binding site that can enhance translation and protein expression. Any of the ribosomal switches, ribosomal binding sites, and terminators described above for the glucose DNA can be used to prepare the insulin DNA.

In one aspect, the insulin promoter in the insulin DNA has SEQ ID NO. 7 or a derivative or variant thereof. In another aspect, the human insulin protein in the insulin DNA has SEQ ID NO. 8 or a derivative or variant thereof.

In another aspect, the insulin DNA comprises the following components in the following sequence: an insulin promoter having SEQ ID NO. 7, a human insulin protein having SEQ ID NO. 8, a ribosomal switch having SEQ ID NO. 3, a ribosomal binding site having SEQ ID NO. 4, a terminator having SEQ ID NO. 5, and a reporter protein.

The glucose and insulin DNA can be synthesized using techniques known in the art (see Sandhu et al., Biotechniques, 12, (1992), 14-16). Primers useful for assembling the glucose and insulin DNA include SEQ ID NOS. 9-19. Overlapping primers are assembled and amplified by PCR to provide the full length sequence of the glucose or insulin DNA. The glucose DNA or insulin DNA is then subsequently cloned into the cloning vector (e.g., pYES, PBSKII). Individual clones are then sequenced and site directed mutagenesis was used to correct mutations in the clones and subsequently sequenced for verification. The amount of glucose DNA and insulin DNA incorporated into the vector can vary. In one aspect, the ratio by volume of glucose DNA or insulin DNA to the vector is from 1:1, 1:2, 1:3 1:4, or 1:5. After the vector comprising the glucose DNA or insulin DNA has been produced, the resulting vector can be incorporated into the host cells using the methods described above.

The host cells comprising the glucose and/or insulin DNA described herein are useful as sensors for quantifying the amount of glucose and insulin in a subject. For example, when the host cell comprising the glucose DNA comes into contact with glucose present in a sample, the host cells will produce fluorescent light in an amount proportional to the amount of glucose present. The same principle applies to the insulin sensor (i.e., host cells comprising insulin DNA). The sample to be evaluated can be any biological material that contains glucose or insulin including, but not limited to, blood, serum, plasma, saliva, and urine. Exemplary procedures for contacting the host cells composed of glucose and insulin DNA described herein are provided in the Examples.

The selection of the reporter protein can vary in the glucose and insulin DNA. For example, the reporter protein can be a yellow fluorescent protein, red fluorescent protein, a green fluorescent protein, and a cyan fluorescent protein. In one aspect, the reporter protein has SEQ ID NO. 6. In the case when host cells contain both the glucose DNA and the insulin DNA, the reporter protein is different for each DNA such that the fluorescence that is produced is different and easily detectable. For example, the glucose DNA can have a reporter protein that produces green fluorescent protein when the host cell comes into contact with glucose, and the insulin DNA can have a reporter protein that produces yellow fluorescent protein when the host cell comes into contact with insulin. Here is possible to detect and quantify the amount of green and yellow fluorescence that is produced, which is ultimately used to calculate the amount of glucose and insulin present in the sample. This embodiment is convenient and cost effective, as only one group of host cells and sample are required to measure both glucose and insulin levels.

The fluorescence produced by the host cells can be detected and quantified using techniques known in the art. For example, spectrophotometers are typically used to measure fluorescence. The Examples provide exemplary procedures for measuring the amount of fluorescence as a result of the expression of the glucose DNA or insulin DNA. After the fluorescence has been quantified, the value is correlated in order to provide a glucose or insulin concentration in the sample. In one aspect, the fluorescence value can be directly correlated with the corresponding glucose or insulin results from clinical data. Thus, a chart or computer program can be used to correlate different fluorescence values to different glucose and insulin concentrations. The Examples provide exemplary methods for correlating fluorescence values with clinical data.

The glucose and insulin sensors described herein have numerous clinical applications. For example, they can be used in analytical labs where it is desirable to test many samples. Alternatively, the sensors can be used in the physician's office or at the subject's home in order to evaluate glucose and insulin levels. In one aspect, described herein is a kit comprising (1) a slide comprising the host cells having the glucose and/or insulin DNA for receiving a sample of blood from a subject, and (2) a device for receiving the slide, wherein the device (i) measures the amount of fluorescence produced when the sample comes into contact with the slide and (ii) correlates the amount of glucose and/or insulin present in the sample.

Figure 9:
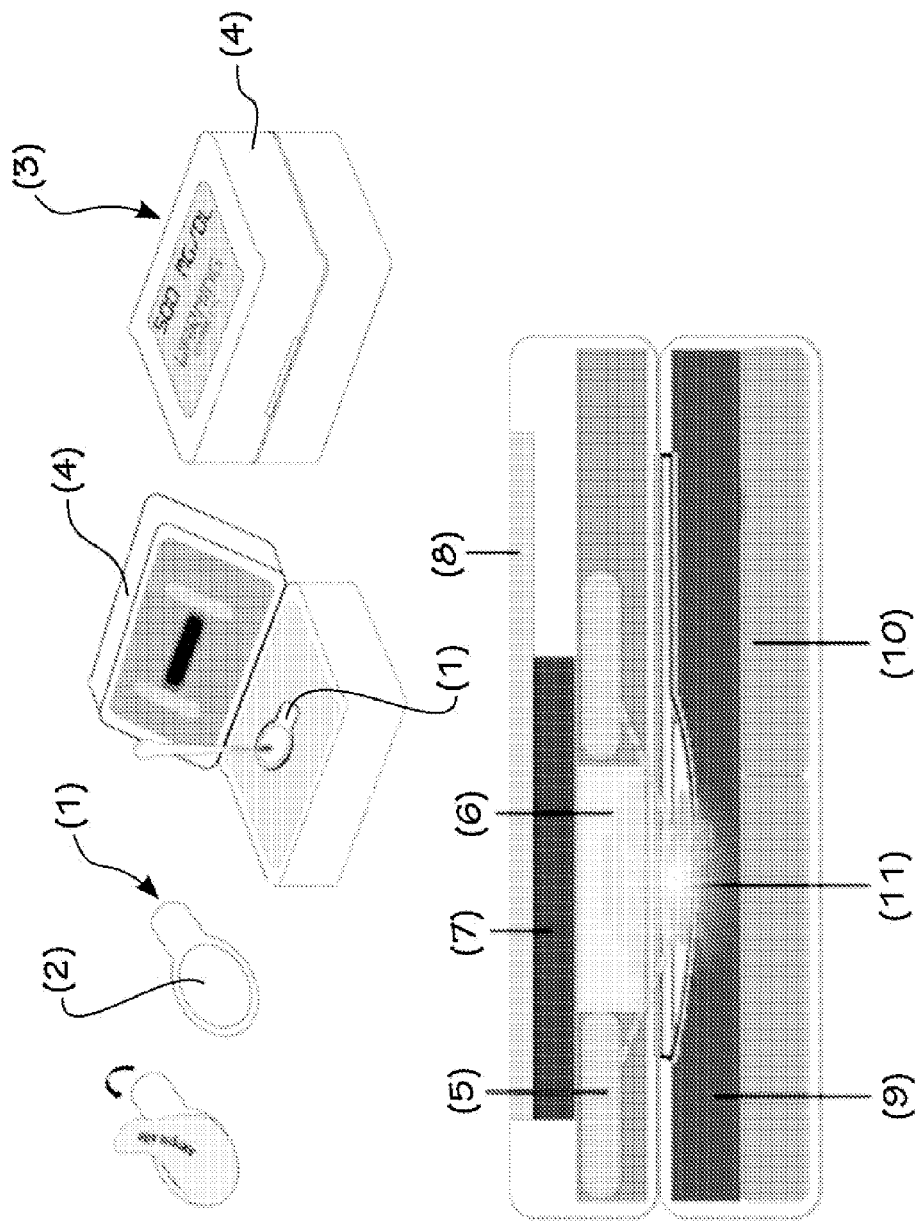
FIG. 9 shows a kit composed of a device and a sensor described herein for use at home or a physician's office.

FIG. 9 depicts an exemplary kit described herein. Slide 1 has on one surface the glucose and/or insulin sensor 2. In one aspect, slide 1 is a disposable concave slide capable of receiving a sample of blood. After a sample of blood is applied to the slide, the slide is placed in a device 3 in sample site 11 that measures the amount of fluorescence produced from the sample on the slide and converts the fluorescence value to a glucose and/or insulin value. Referring to FIG. 9, the lid of the box 4 is fitted with a light source 5 and filter and detector 6 to read fluorescence. A transducer 7 converts the fluorescence values to a digital glucose and/or insulin value that is displayed on screen 8. The device can be fitted with a vibrator 9 in order to ensure that the sample is adequately mixed with the sensor on slide 1. The device can be battery operated for convenience (10 in FIG. 9).

The sensors and methods described herein possess numerous advantages over current glucose and insulin meters. The sensors described herein are able to determine lower levels of glucose (below (<20 mg/dl) than the levels detected by conventional clinical and/or commercial methods. The sensors can measure higher levels of glucose in blood (up to 500 mg/dl), which is comparable to conventional technologies. The sensors can detect a wide range of insulin levels as well (0 to 250 or more µIU/ml). In addition to sensitivity, the sensors described herein can accurately detect different levels of glucose and insulin in blood quicker than current meters available to the public.

The manufacture and use of the sensors is low cost and easy to apply. The sensors are versatile in that they can determine both glucose and insulin in blood simultaneously. This is not the case with technologies, where to different samples and tests are required. The sensors also require a small drop of about 3 µl for analysis. Thus, the sensor can be reused for a longer period of time, which extends the use of the sensor and ultimately reducing costs to the subject.

Due to the higher sensitivity of the sensors, it is possible to differentiate between different stages of diabetes in patients earlier when compared to using conventional methods and technologies. The sensors are designed to be used by physicians and non-physicians in the office or at home with no training involved.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Blood Samples. Samples were taken at different volumes (5,000, 3,000, 1,500, 1,000, 100 and 3 µl) from different individuals, including diabetes, pre-diabetes, and non-diabetic patients. These samples were used immediately and or kept in the refrigerator few minutes until use. Aliquots of 2 ml (amount of blood used) were used for analysis, each time.

Construction of DNA Sensor. Yeast cells (*Saccharomyces cerevisiae* ATCC 200892) were transformed to be able to hold the new synthesized DNA genetic parts assembled in plasmid vectors (genetic parts sequences such as glucose ADH1 promoter, snf3 glucose receptor, insulin promoter, insulin protein, riboswitch tc aptamer, and different reporter protein such as cyanin, Red and yellow Fluorescent proteins to produce differential fluorescent gene expression based on glucose and insulin concentrations, and also to ensure assembly, and pYES plasmid as backbone or vector). The methods disclosed in Leonard G. Davis, Michael Kuehl, James F. Battey. 1995. Basic Methods In Molecular Biology. McGraw-Hill Professional; 2nd edition, and Gietz, R. D. and R. H. Schiestl. 2007. Nature Protocols. Quick and easy yeast transformation using the LiAc/SS carrier DNA/PEG method. Vol 2. 35-37. doi:10.1038/nprot.2007.14 were used to transform the yeast with the DNA.

Two different types of sensors, one for glucose and one for insulin in blood, were constructed, as follows:

Sensor for Insulin in Blood. The sensor for detection of insulin in blood, was constructed by assembling plasmid including parts sequences of Insulin promoter (401 bps), Human insulin protein (333 bps) and ribosomal switch (76 bps), Ribosomal Biding Site (RBS, 29 bps), Terminator (129 bps) and reporter protein (979 bps) that produces fluorescence.

Sensor for Glucose in Blood. The sensor was constructed to determine the concentration of glucose in blood. Different gene parts and proteins, include plasmid (pBSKII), sequences of ADH1 glucose promoter (1445 bps), snf3 glucose protein receptor (2244 bps) and ribosomal switch (76 bps), Ribosomal Biding Site (RBS, 29 bps), Terminator (129 bps) and reporter protein (979 bps) that produce fluorescence.

Two different transformed yeast cells (i.e., DNA sensors) were obtained. Different types of reporter fluorescent proteins were used (yellow fluorescent protein, red Fluorescent protein, green fluorescent protein and cyan fluorescent protein) for all transformed yeast cells or devices. However, the cyan fluorescent protein was the best to express the fluorescence (mostly green or light blue in color). When no reporter fluorescent protein was assembled no fluorescence was observed. (Tables 1 and 2).

In this protocol, PCR was used to enhance DNA concentration using standard 5332 eppendorf thermocycler (Eppendorf North America. 102 Motor Parkway, Hauppauge, N.Y. 11788) with specific sequence primers (SEQ ID NOS. 9-19), and the standard method for amplification (Sambrook et. al, 1989); digestion and ligation were used to ensure assembly of DNA synthesized parts using promega restriction enzymes and reagents (promega PCR master mix, restriction enzymes: XhoI, KpnI, XbaI EcoRI, BamHI and HindIII, Alakaline Phosphatase and quick ligation kit among others). DNA was quantified using a nano view spectrophotometer GE nanospectrophotometer (GE Healthcare Biosciences P.O. Box 643065 Pittsburgh, Pa. 15264-3065), and also regular standard UV/visual spectrophotometer within a 260/280 wavelength (GE Healthcare Biosciences P.O. Box 643065 Pittsburgh, Pa. 15264-3065), to verify final ligations. DNA was visualized and purified with electrophoresis using standard Thermo EC (EC-150) electrophoresis equipment.

Figure 2:
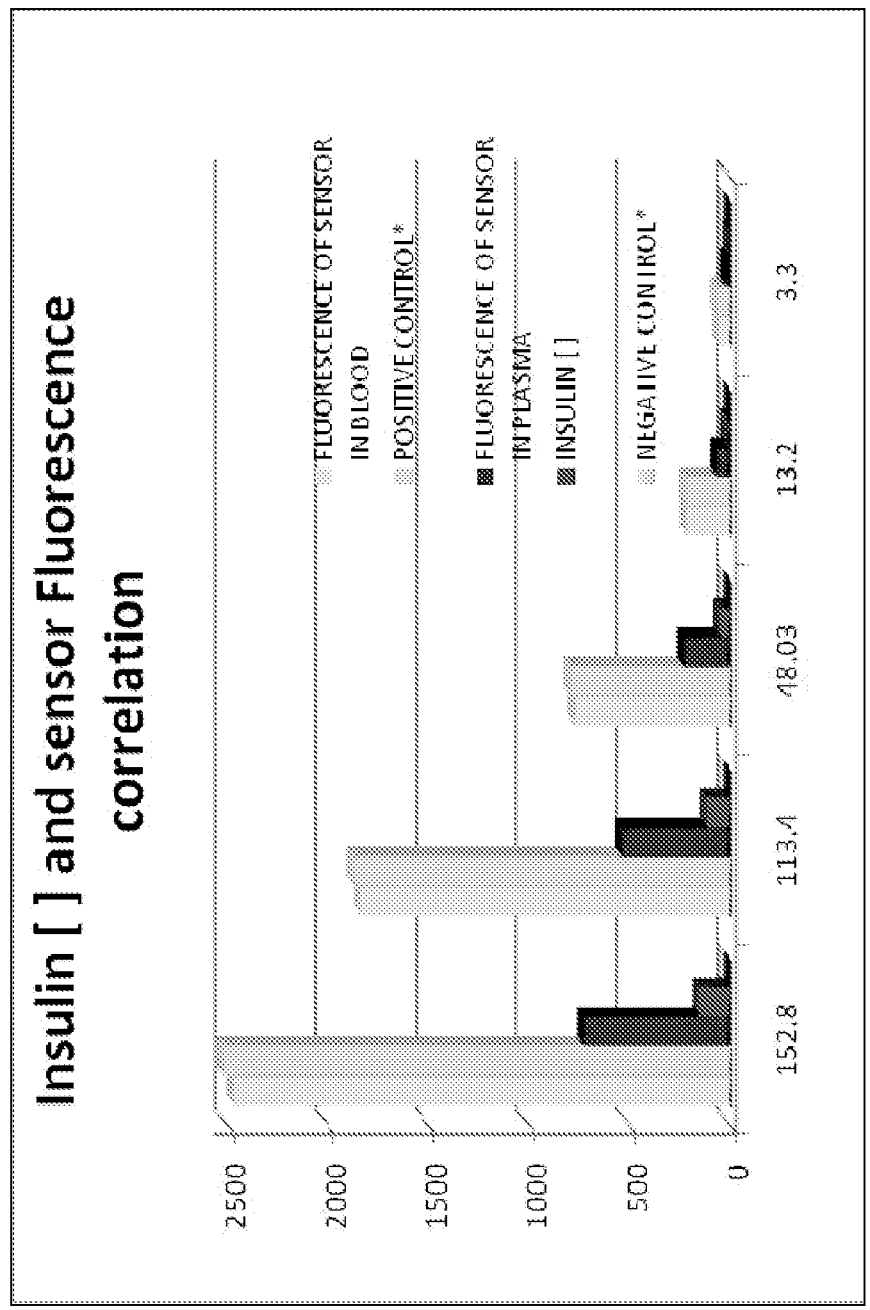
FIG. 2 shows (A) the equivalent proportion correlation of sensor fluorescence and clinical insulin values; and (B) the equivalent proportion correlation of the DNA sensor and fluorescence when testing for insulin in different patients including uncontrolled diabetic, controlled diabetic, pre-diabetic, non diabetic and hypoglycemic patients.
Figure 2:
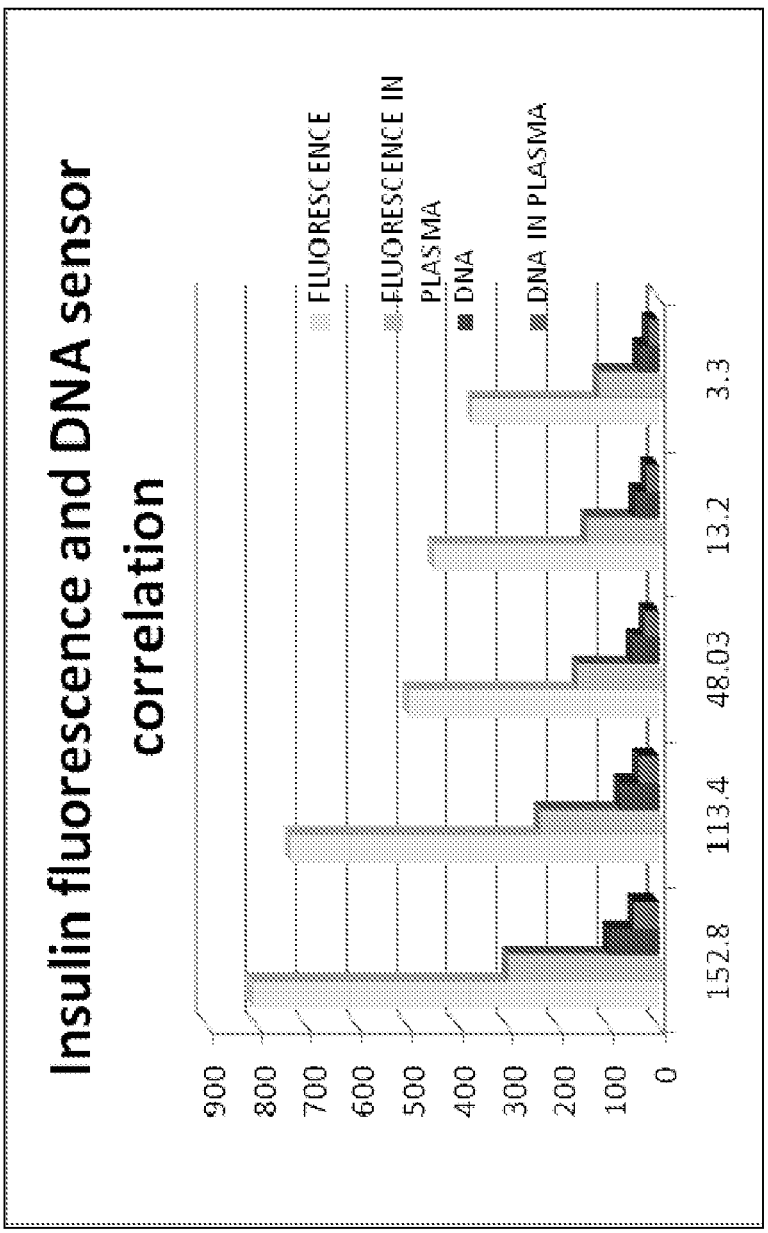
Figure 3:
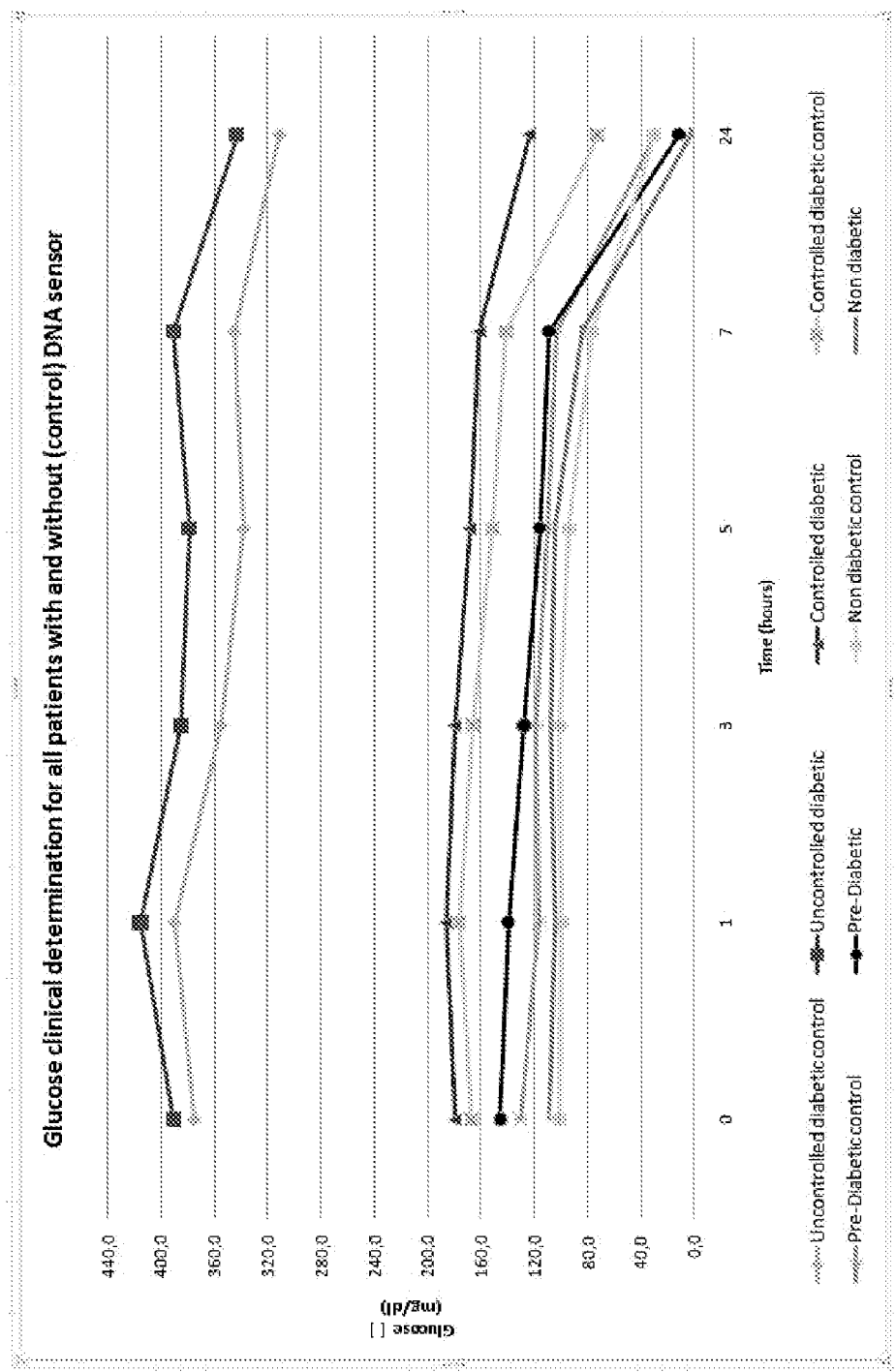
FIG. 3 shows the sensibility of a sensor described herein in comparison with conventional methods (differences in the ability to measure clinical glucose, in different diabetic and non-diabetic patients within 24 hours).
Figure 4:
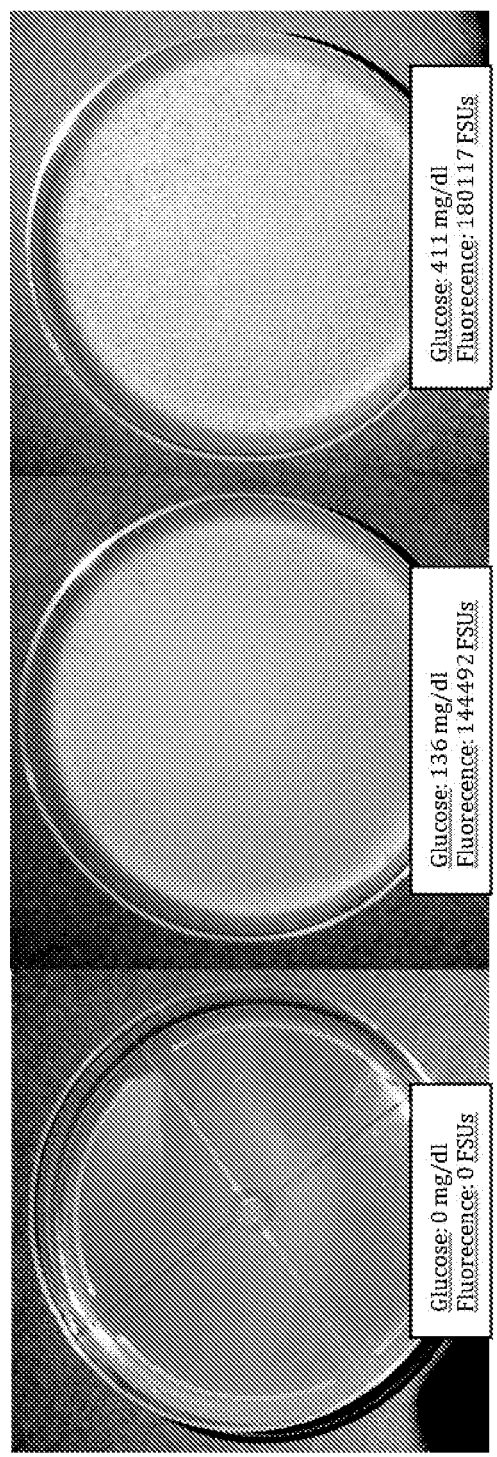
FIG. 4 shows a yeast device sensor with colonies fluorescing after exposure to different glucose concentrations in vitro assay.
Figure 5:
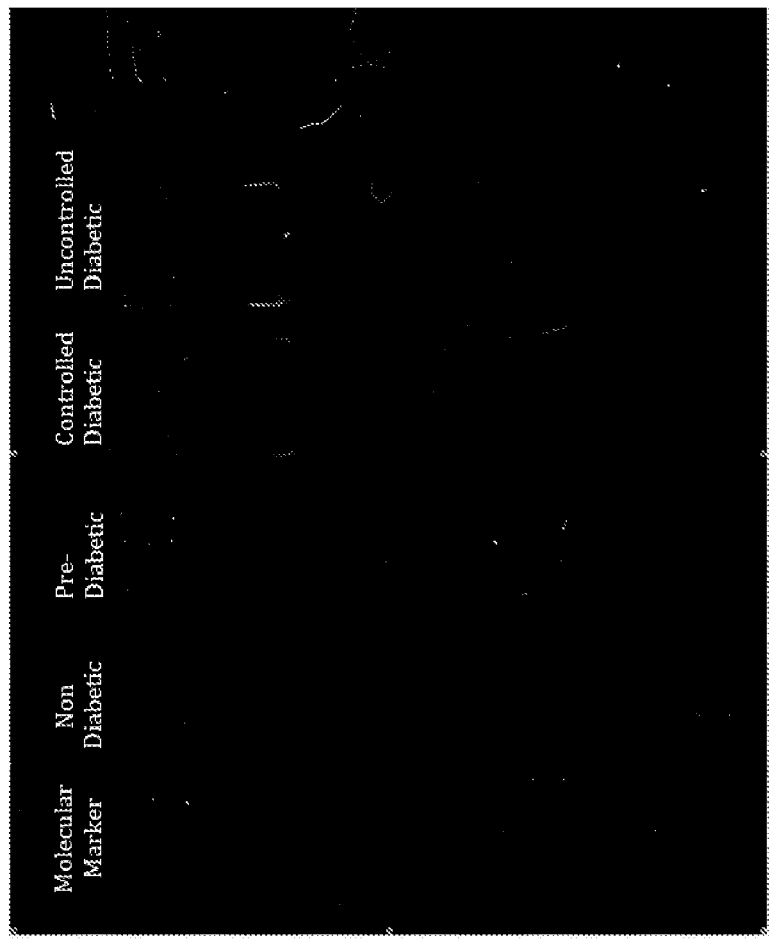
FIG. 5 shows the electrophoresis bands of a sensor described herein, expressing different fluorescence after exposure to blood samples from different patients. In vivo test. The bans in the gel indicate the following from left to right. Lane 1. Molecular DNA marker (1 Kb). Lane 2. Sensor described herein expressed in normal patient sample. Lane 3. Sensor described herein expressed in Pre-diabetic patient sample. Lane 4. Sensor described herein expressed in controlled diabetic patient sample. Lane 5. Sensor described herein expressed in uncontrolled diabetic patient sample.

DNA expression was determined by fluorescence of the transformed cells expressed in Florescent units (FSUs) according the company protocol using the promega 20/20 illuminometer, with the blue fluorescence module within the 450/600 wave length. The DNA sensor was only fluorescent in blood when the transformed yeast cells or device contained the denoted parts and plasmids that were specific for glucose or insulin, as compared to control non-transformed yeast cells that do not contain the glucose or insulin DNA (Tables 1 and 2 and FIG. 5). The direct relationship between sensitivity of the DNA sensor and fluorescence with glucose or insulin concentrations was also demonstrated (FIGS. 1B and 2B). The efficacy of the sensor was assayed in vitro in an agar plate and liquid broth where the transformed yeast cells were growing (FIG. 4) and in vivo, using blood drop and other volume samples, in which the fluorescence was determined based on the concentration of glucose and insulin (FIGS. 1 and 2).

TABLE 1

Differential DNA sensor fluorescence and DNA determinations based on clinical glucose concentration for different types of diabetic patients. Uncontrolled diabetic, controlled diabetic, pre-diabetic, non-diabetic and hypoglycemic patients.

| Patient | Fluorescence (FSUs) | Glucose (mg/dl) | DNA (ng/µl) |
|---|---|---|---|
| Uncontrolled diabetic | 180117 ± 2069.5 | 411 ± 3.5 | 85 ± 4.8 |
| Uncontrolled diabetic control* | 0 | 387 ± 2.9 | 25 ± 0 |
| Uncontrolled diabetic plasma | 90647 ± 542 | 411 ± 3.5 | 30.7 ± 1.3 |
| Controlled diabetic | 174512.8 ± 3532.5 | 185.7 ± 1.9 | 77 ± 1.1 |
| Controlled diabetic control* | 0 | 178.2 ± 2.5 | 11.5 ± 2.3 |
| Controlled diabetic plasma | 88135 ± 1204 | 185.7 ± 1.9 | 23.7 ± 2.4 |
| Pre-diabetic | 144492.4 ± 709 | 135.9 ± 5.1 | 52.5 ± 2.6 |
| Pre-diabetic control* | 0 | 122.4 ± 2.1 | 23 ± 1.6 |
| Pre-diabetic plasma | 76328 ± 784 | 135.9 ± 5.1 | 16.15 ± 1.5 |
| Non diabetic | 115409.4 ± 540.7 | 107.1 ± 5.3 | 47 ± 0.6 |
| Non diabetic control* | 0 | 100.2 ± 3.1 | 18.5 ± 0.6 |
| Non diabetic plasma | 58439 ± 2131 | 107.1 ± 5.3 | 14.5 ± 1 |
| Hypoglicemic | 79917 ± 3066.3 | 12.5 ± 3.1 | 39 ± 7.1 |
| Hypoglicemic control* | 0 | <20 ± 0 | 15.4 ± 3.1 |
| Hypoglycemic plasma | 37194 ± 341 | 12.5 ± 3.1 | 12 ± 0.7 |

*Control: patient sample with no sensor device (water instead) or no fluorescent reporter protein assembled to it.

TABLE 2

Differential DNA sensor fluorescence and DNA determinations based on clinical Insulin concentration for different types of diabetic patients. Uncontrolled diabetic, controlled diabetic, pre-diabetic, non-diabetic and hypoglycemic patients.

| Patient | Fluorescence (FSUs) | Insulin (µIU/ml) | DNA (ng/µl) |
|---|---|---|---|
| Uncontrolled diabetic | 334121.6 ± 3811.9 | 48.03 ± 1.4 | 85 ± 4.8 |
| Uncontrolled diabetic control* | 0 | 48.03 ± 1.4 | 25 ± 0 |
| Uncontrolled diabetic plasma | 85371 ± 1532 | 48.03 ± 1.4 | 36.5 ± 2 |
| Controlled diabetic | 378019 ± 3981.6 | 152.8 ± 0.3 | 77 ± 1.1 |
| Controlled diabetic control* | 0 | 152.8 ± 0.3 | 11.5 ± 2.3 |
| Controlled diabetic plasma | 97328 ± 903 | 152.8 ± 0.3 | 27.3 ± 0.8 |
| Pre-diabetic | 337661.8 ± 4711.1 | 113.4 ± 0.1 | 52.5 ± 2.6 |
| Pre-diabetic control* | 0 | 113.4 ± 0.1 | 23 ± 1.6 |
| Pre-diabetic plasma | 92186 ± 1137 | 113.4 ± 0.1 | 18.9 ± 1.2 |
| Non diabetic | 210546.7 ± 2093.7 | 3.3 ± 1.2 | 47 ± 0.6 |
| Non diabetic control* | 0 | 3.3 ± 1.2 | 18.5 ± 0.6 |
| Non diabetic plasma | 27328 ± 2231 | 3.3 ± 1.2 | 15.2 ± 1.3 |
| Hypoglicemic | 275659 ± 629.8 | 13.2 ± 0.4 | 39 ± 7.1 |
| Hypoglicemic control* | 0 | 13.2 ± 0.4 | 15.4 ± 3.1 |
| Hypoglycemic plasma | 60397 ± 395 | 13.2 ± 0.4 | 11.3 ± 0.3 |

*Control: patient sample with no sensor device (water instead) or no fluorescent reporter protein assembled to it.

In Vitro Yeast Growth and DNA Detection of Glucose and Insulin in Culture Media. Yeast cells were grown in YPD commercial media from 8 to 18 hours until they reached an OD of 1. They were sub-cultured in sterile-deionized water in different glucose blood equivalent concentrations (from 0 to 500 mg/dl) and or different proportion of insulin (1:1, 1:2, 1:3, 1:4, 0:1) during different time intervals ranging from 1 hour to 48 hours. Fluorescence and DNA were determined for all samples and correlated with glucose and insulin concentrations (FIGS. 1B and 2B). The fluorescence is provided in FSUs according to the protocol of the company 20/20 promega fluorometer.

Figure 6:
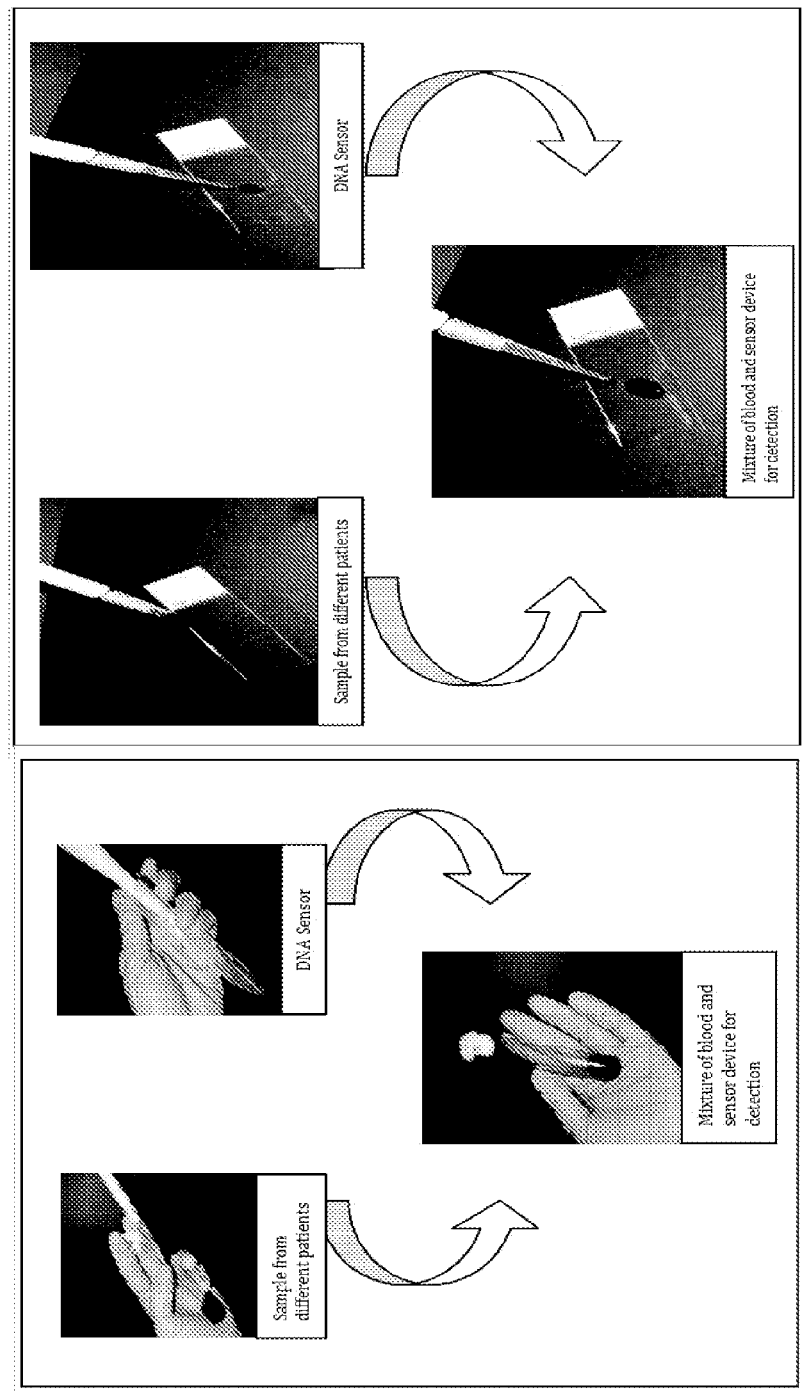
FIG. 6 shows steps for preparing blood samples for glucose and or insulin detention after mixed with the sensor described herein indicating the process for preparing the analysis of glucose and or insulin mixed with the sensor for detection. Time course experiments showed no blood alteration after mixing with the sensor.

The In Vivo Determinations of Glucose and Insulin. Blood samples obtained from patients as described above were mixed with the glucose or insulin DNA sensor with an initial concentration of 10*3 cells (Optical Density: 0.09). The mixture was mixed and vortexed very lightly (15 rpm) for different times in order to ensure full mixture (FIG. 6). Different levels of fluorescence were produced from this mixture depending on the concentration of glucose and insulin (e.g. from 12 to 450 mg/dl for glucose and from 3 to 150 µIU/ml for insulin, Tables 1 and 2), at different times (30, 5, 3 and 1 minutes and 24, 12, 7, 5, 3, 1 hours), with 1 minute was the preferred time. This fluorescence is provided in FSUs according to the protocol of the company 20/20 promega fluorometer.

The results are presented by the mean with the respective standard deviation, 4 replicates of blood sample for each treatment were used each time in order to have reliable statistical analysis. The statistical analysis was based on the program SigmaPlot-Scientific Data Analysis and Graphing Software. The results are expressed as mean and standard deviation and difference within treatments, and with an α of 0.005.

Glucose and insulin values for all samples were determined by glucose oxidation method and electrochemiluminescence, respectively. The blood samples for insulin detection by the DNA sensor were also subjected to clinical analysis in the Hormonal Research Laboratory in Bogota, Colombia. The concentration of insulin obtained from this laboratory was compared to the concentration of insulin obtained from the fluorescence of the yeast DNA sensor mixed with the blood samples. Blood samples not mixed with the DNA sensor were the control. Other controls included the DNA sensor mixed with sterile-deionized water or with blood plasma. There was no fluorescence in the mixture of the DNA sensor with water. Some fluorescence, approximately half of the produced in blood or pure solutions of glucose and insulin was observed, which showed similar proportions in the mixture of the DNA sensor and the plasma (Figures and Tables 1 and 2). The fluorescence units were directly correlated with the corresponding glucose or insulin results from the clinical data. It represents the expression of the reporter protein assembled in the different plasmid parts of the DNA sensor.

Analysis of Protein Expression in Yeast.

Figure 7:
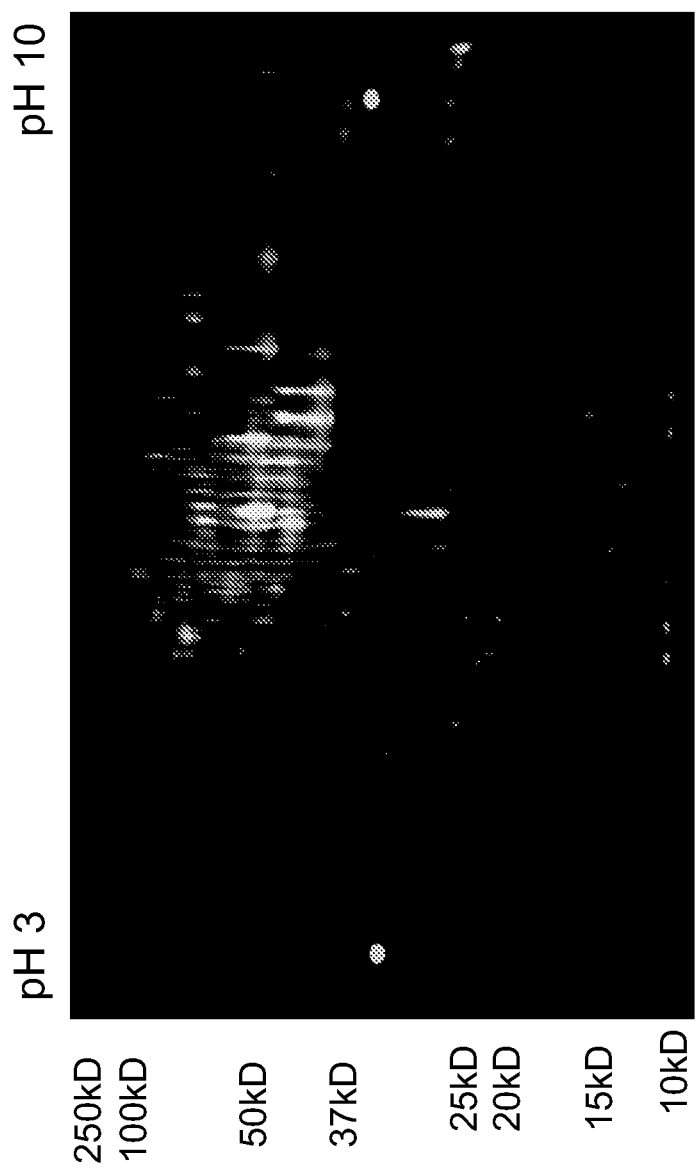
FIG. 7 shows two dimensional (2D-DIGE) gel showing fluorescence of the proteins produced by the sensor described herein at different intensities. The brightest spots were selected for analysis under HPLC mass spectrometry and laser identification.
Figure 8:
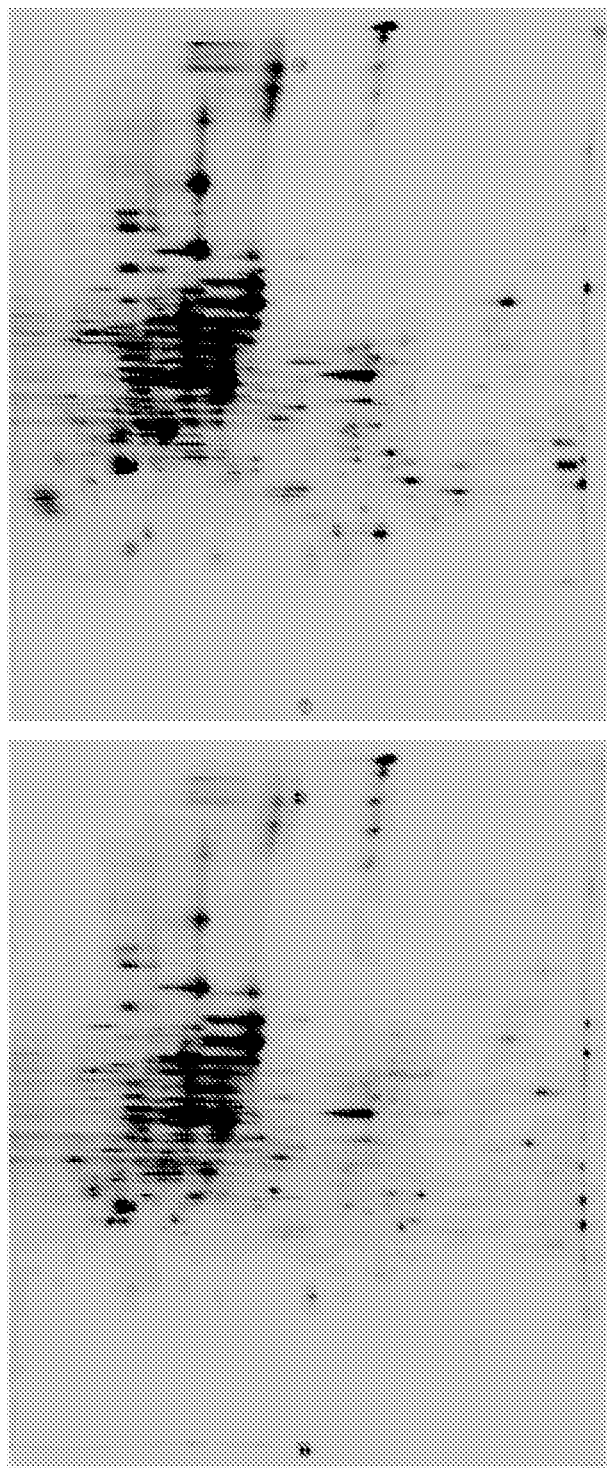
FIG. 8 shows different protein spots selected from the brightest protein spot, after using laser beams. The control gel (no transformed yeast) is in the left of the transformed gel. In the control gel, there are down-regulated proteins, and on the right gel the transformed or treated yeast gel the up-regulated proteins. The proteins are expressed by the degree of intensity. Experimental gel (DNA sensor) shows the brightest spots.

The difference in expression can be seen in the 2D DIGE gels shown in FIG. 7. Six spots of each representing increased or decreased amount of protein from the gels were analyzed and identified. Eight of the identified proteins are shown in a Table 3. It was observed that nucleotides and amino acids were synthesized. Proteins were regulated and expressed in higher concentrations of glucose and insulin.

TABLE 3

List of main proteins produced by the Sensor devices after MALDI, LASER and HPLC mass spectrometry analysis. Identification of protein spots showing changes in protein expression. Production of the proteins confirmed that the transformed sensor device was prepared properly, and the assemblage of the different genetic components occurred effectively.

| Spot No. | Name | Accession No. | Change | Volume ratio (fold) | Description |
|---|---|---|---|---|---|
| 1225 | S-adenosylmethionine synthase 2 | P19358.3 | Increased | 3 | Catalyzes the formation of S-adenosylmethionine from methionine and ATP. Amynoacid byosinthesys. Glucose and insulin increased cellular homocysteine production primarily by its inhibition of transsulfuration |
| 1061 | Pyruvate kinase 1 | P00549.2 | Increased | 3 | Involved in glycolysis. It catalyzes the transfer of a phosphate group from phosphoenolpyruvate (PEP) to ADP, yielding one molecule of pyruvate and one molecule of ATP |
| 1843 | Phosphomanno-mutase | P07283.1 | Increased | 3 | Transfer of phosphate groups within a molecule. D-glucose 1,6-bisphosphate cofactor dependent. Phosphoglucomutase activity in some tissues |
| 1568 | Protein disulfide isomerase | P17505.2 | Increased | 2 | Catalyzes the formation and breakage of disulfide bonds between cysteine residues within proteins as they fold. Glucose regulated proteins |
| 1126 | Hexokinase 1 | P04806.2 | Increased | 7 | phosphorylates a six-carbon sugar, to a hexose phosphate. Glucose is the most important substrate of hexokinases, and glucose-6-phosphate is the product |
| 1923 | Translationally-controlled tumor protein analog (TCTP | P3569.1 | Increased | 8 | Anti-apoptotic protein. May contribute to explain the different effects exerted by palmitate and oleate on β-cell function. Inhibiting down-regulation of enzymes of glycolysis |
| 803 | Glutamate synthase | Q12680.2 | Decreased | 14 | Participates in glutamate metabolism and nitrogen metabolism. In S. cerevisiae. Glucose exerts strong catabolite repression on the enzymes required for respiration and on the enzymes of the tricarboxylic acid cycle beyond those required for the synthesis of 2-ketoglutarate. It occurs in bacteria and plants but not animals |
| 575 | Glycinamide ribonucleotide synthetase | P07244.1 | Decreased | 9.05 | De novo purIn biosynthesis. Inhibited when high levels of adoMet are present possibly due to phosphate produced during enzyme reaction. |

Analysis Cost Estimation. Cost per sample was estimated, including depreciated value of equipment, cost of materials required to take the sample, and price of reagents in the sensor. The cost per sample is based on statistical values of 700 samples monthly for glucose and 500 for insulin including measurement of reference and standards daily, downtime and equipment capacity.

Both apparatuses in the case of the glucose sensor are considered manual. In both cases, one can afford on semi and automated equipment, which is more expensive but can create more capacity for sampling and lowering the price per sample. The biggest difference for glucose analysis is in the use of two apparatuses for the conventional method and material costs required to take and store the sample (Table 4). In the case of the insulin cost analysis, the cost of reagents makes a big difference in determining price per sample (Table 5).

TABLE 4

Cost of glucose analysis without utility using the glucose sensor in comparison to existing technology in the market.

|  | Cost analysis/ sample/person in clinical laboratories | Cost analysis/ sample/person in personal or home monitoring methods |
| --- | --- | --- |
| DNA sensor | $0.5 USD | $0.5 USD |
| Conventional analysis | $1.3 USD | $0.4-1 USD |

TABLE 5

Cost of insulin analysis without utility using the insulin sensor in comparison to existing technology in the market.

|  | Cost analysis/ sample/person in clinical laboratories | Cost analysis/ sample/person in personal or home monitoring methods |
| --- | --- | --- |
| DNA sensor | $0.5 USD | $0.5 USD |
| Conventional analysis | $11.15 USD | N.A* |

*Not available. No knowledge of its existence

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A sensor comprising a host cell comprising (1) a first DNA, wherein the first DNA comprises the following components in the following sequence: a glucose promoter that has at least 95% homology to SEQ ID NOS: 1 and 30-32, a glucose protein receptor that has at least 95% homology to SEQ ID NOS: 2 and 20-29, a ribosomal binding site, terminator, and a first fluorescence reporter protein; and (2) a second DNA, wherein the second DNA comprises the following components in the following sequence: an insulin promoter that has at least 95% homology to SEQ ID NOT: 7, a human insulin protein that has at least 95% homology to SEQ ID NO: 8, a ribosomal binding site, a terminator, and a second fluorescence reporter protein.

2. The sensor of claim 1, wherein the first DNA further comprises a ribosomal switch between the glucose protein receptor and the ribosomal binding site.

3. The sensor of claim 1, wherein the second DNA further comprises a ribosomal switch between the human insulin protein and the ribosomal binding site.

4. The sensor of claim 1, wherein the host cell comprises yeast or *E. coli*.

5. The sensor of claim 1, wherein the first and second DNA comprises a vector.

6. The sensor of claim 1, wherein the first and second DNA comprises a plasmid.

7. The sensor of claim 2, wherein the first DNA comprises a glucose promoter having SEQ ID NO: 1, a glucose protein receptor having SEQ ID NO: 2, a ribosomal switch having SEQ ID NO: 3, a ribosomal binding site having SEQ ID NO: 4, a terminator having SEQ ID NO 5, and a first fluorescence reporter protein having SEQ ID NO: 6.

8. The sensor of claim 3, wherein the second DNA comprises an insulin promoter having SEQ ID NO: 7, a human insulin protein having SEQ ID NO: 8, a ribosomal switch having SEQ ID NO: 3, a ribosomal binding site having SEQ ID NO: 4, a terminator having SEQ ID NO: 5, and a second fluorescence reporter protein having SEQ ID NO: 6.

9. A method for quantifying the amount of glucose and insulin in a subject, the method comprising:
 (a) obtaining a sample from the subject;
 (b) contacting the sample with a host cell of claim 1
 (c) measuring the first fluorescence and second fluorescence produced by the host cell.

10. A kit comprising (1) a slide comprising the host cell of claim 1 for receiving a sample of blood from a subject, and (2) a device for receiving the slide, wherein the device measures the amount of fluorescence produced when the sample comes into contact with the slide.

* * * * *

SEQUENCE LISTING

<160> NUMBER OF SEQ ID NOS: 36

<210> SEQ ID NO 1
<211> LENGTH: 1445
<212> TYPE: DNA
<213> ORGANISM: Saccharomyces serivisiae

<400> SEQUENCE: 1

```
aagaaatgat ggtaaatgaa ataggaaatc aaggagcatg aaggcaaaag acaaatataa      60
gggtcgaacg aaaaataaag tgaaaagtgt tgatatgatg tatttggctt tgcggcgccg     120
aaaaaacgag tttacgcaat tgcacaatca tgctgactct gtggcggacc cgcgctcttg     180
ccggcccggc gataacgctg ggcgtgaggc tgtgcccggc ggagtttttt gcgcctgcat     240
tttccaaggt ttaccctgcg ctaagggcg agattggaga agcaataaga atgccggttg      300
gggttgcgat gatgacgacc acgacaactg gtgtcattat ttaagttgcc gaaagaacct     360
gagtgcattt gcaacatgag tatactagaa gaatgagcca agacttgcga gacgcgagtt     420
tgccggtggt gcgaacaata gagcgaccat gaccttgaag gtgagacgcg cataaccgct     480
agagtacttt gaagaggaaa cagcaatagg gttgctacca gtataaatag acaggtacat     540
acaacactgg aaatggttgt ctgtttgagt acgctttcaa ttcatttggg tgtgcacttt     600
attatgttac aaatatggaag ggaactttac acttctccta tgcacatata ttaattaaag    660
tccaatgcta gtagagaagg ggggtaacac ccctccgcgc tcttttccga ttttttttcta    720 aaccgtggaa tatttcggat atccttttgt tgtttccggg tgtacaatat ggacttcctc     780
ttttctggca accaaaccca tacatcggga ttcctataat accttcgttg gtctccctaa     840
catgtaggtg gcggagggga gatatacaat agaacagata ccagacaaga cataatgggc     900
taaacaagac tacaccaatt acactgcctc attgatggtg gtacataacg aactaatact     960
gtagccctag acttgatagc catcatcata tcgaagtttc actaccctttt tccatttgc    1020 catctattga agtaataata ggcgcatgca acttcttttc tttttttttc ttttctctct   1080
cccccgttgt tgtctcacca tatccgcaat gacaaaaaaa atgatggaag acactaaagg   1140
aaaaaattaa cgacaaagac agcaccaaca gatgtcgttg ttccagagct gatgaggggt   1200
```

```
atcttcgaac acacgaaact ttttccttcc ttcattcacg cacactactc tctaatgagc    1260
aacggtatac ggccttcctt ccagttactt gaatttgaaa taaaaaaagt ttgccgcttt    1320
gctatcaagt ataaatagac ctgcaattat taatcttttg tttcctcgtc attgttctcg    1380
ttcccttcct tccttgtttc tttttctgca caatatttca agctatacca agcatacaat    1440
caact                                                                1445
```

<210> SEQ ID NO 2
<211> LENGTH: 2244
<212> TYPE: DNA
<213> ORGANISM: Pichia stipitis

<400> SEQUENCE: 2

```
atgtggaaat ttctagaagc tctactttac gacaacacca tcgaagaaga atactacagg      60
aaaatccgtc aaaagtcctc ctccaagtcg gctgtaatcg taggtcttgt agctgccgtg     120
ggaggctttt tgtatgggta cgatacggga ctcatcaacg acttgctaga atgagatac     180 gtctacgaaa actttccaga aaatctgcat tcgttcacat cacatgaacg agcgttgatt     240
acggctgtgt tatcgctcgg aacattcata ggagctctca tagcgcctct tatctccgac     300
aactatggcc ggaagttttc catcattgtc tcttccggtc tcattttcaa cgcaggcaac     360
attttgcaaa tcgcatcaac aaacgtagca ttgctttgcg ttggtagagc gatctcgggt     420
gtatctgtag gcattctttc ggccattgta cccttgtacc aagctgaagc ttctcccaaa     480
tgggtcagag gttccgtcgt tttcacatat caatgggcca ttacttgggg cttgttgata     540
gcgagtgccg tctgtcaagg cactcgaaaa atgaccaatt ctggctcata tcggatcccc     600
gtgggcctcc agtttctctg ggctcttatc ttgtacacgg ggatgctttt cttgcccgaa     660
agtccccgtt attatgttca aaagacgat cttcagaaag ctctagatag tttgtcgaag     720
ttgcgaaagt tgccccaga cgacgctgat tgatagagg agttggtgga aatcaaggct     780
aactacgact acgagttgtc gtatggtaag accaactatc ttgattgctt ccgtagtgga     840
ggaggaagac acaagcaggt gttgcgaatg ttcactggaa tcggtgctca actctttcag     900
cagtgttcag gcatcaactt catcttctac tatggtgtca acttcttctc cagcaccggc     960
atccagaact tttacatcat gtccttcgtg acgtatttgg tcaacactat cttcacaatc    1020
cccggaataa ttctagtgga tacgataggc aggcgacagt tgctcctatg gggtggcgta    1080
ggcatgtcta ccgcgaactt cataattgcg attacgggag tcagtatctc cagtaaggaa    1140
accagttcga ttctaagcgt ctgttttttcg tgtgtgttca tagcgttttt cgccagttcg    1200
tggggtggat gtgtatgggc actcacttct gatatatacg gtattagtat cagacagaga    1260
gccatatcca tcactacagc cacgaactgg ttggtcaact tcatctttgc ctacataaca    1320
ccgtatctca tcgatacggg acaccatact gcagctatag gaaacaaaat cttctttatc    1380
tggggaggtt gtaacgctgc cggtgtcgtt ttcgtctact tcactgtcta cgaaacaaag    1440
ggattgaagt tggaggaaat tgattatatg tacgctcatt gtgacaatgc gagaaagtcc    1500
accgagttca gtcgaccaa atcgattac actagattgg acgagaacta caacgctgta    1560
ccctgggatc ctccttatcc atcaacaacg agctcatcgc ctccttctaa catcaacgag    1620
aaggaccttt catcttctga tcccaaccaa gacgtcaatg tacatagtga caacaacgag    1680
tttgttccat tgtacaacaa caaaaaactt ccaaataatc ctacaaacac caacaaaaac    1740 gacatccacca tcattcccta caacaatatc attctgccgt cgttatcatc gaactccgag    1800
ccctcttctg ctgcttcgtc aattctcaac aacagattcc accacaactc tgtctcgact    1860
```

```
acaaacaacg tctctgtatc tacatctaac cctggccaat cttctggtca aggtacagct      1920
tccaacgact acttgctgta tttggatagt ttgaagtctg agtacggaag tccacctcac      1980
tacaataacg acacactaca ccagcagcac accaaccaat cgaactccaa gggttctgct      2040
acagacagaa acagcagcat cactgctagc aacattcacc atactcatag caacatcacc      2100
agcaacatta ataaccataa tagtaataac attaataaca gtataaccaa caattcgacc      2160
acgattattg ccacgccata cttcaaccag cctccaccag actcttccga tgaagaagac      2220
gaagacgagg acgaagaaga atag                                             2244

<210> SEQ ID NO 3
<211> LENGTH: 76
<212> TYPE: RNA
<213> ORGANISM: Saccharomyces serivisiae

<400> SEQUENCE: 3
ugcuuaaggc cuaaaacaua ccagaucgcc acccgcgcuu uaaucuggag aggugaauac      60
gaccaccuag gccaaa                                                     76

<210> SEQ ID NO 4
<211> LENGTH: 29
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t

<400> SEQUENCE: 4
tctagagaaa gannngannn tactagatg                                        29

<210> SEQ ID NO 5
<211> LENGTH: 129
<212> TYPE: DNA
<213> ORGANISM: Artificial sequence
<220> FEATURE:
<223> OTHER INFORMATION: Synthetic construct

<400> SEQUENCE: 5
ccaggcatca ataaaacga aaggctcagt cgaaagactg ggcctttcgt tttatctgtt       60
gtttgtcggt gaacgctctc tactagagtc acactggctc accttcgggt gggcctttct     120
gcgtttata                                                             129

<210> SEQ ID NO 6
<211> LENGTH: 979
<212> TYPE: DNA
<213> ORGANISM: Artificial sequence
<220> FEATURE:
<223> OTHER INFORMATION: Synthetic construct

<400> SEQUENCE: 6
tccctatcag tgatagagat tgacatccct atcagtgata gagatactga gcactactag      60
agaaagagga gaaatactag atggtgagca agggcgagga gctgttcacc ggggtggtgc     120
ccatcctggt cgagctggac ggcgacgtga acggccacaa gttcagcgtg tccggcgagg     180
gcgagggcga tgccacctac ggcaagctga ccctgaagtt catctgcacc accggcaagc     240
```

```
tgcccgtgcc ctggcccacc ctcgtgacca ccctgacctg gggcgtgcag tgcttcagcc    300
gctaccccga ccacatgaag cagcacgact tcttcaagtc cgccatgccc gaaggctacg    360
tccaggagcg caccatcttc ttcaaggacg acggcaacta caagacccgc gccgaggtga    420
agttcgaggg cgacaccctg gtgaaccgca tcgagctgaa gggcatcgac ttcaaggagg    480
acggcaacat cctggggcac aagctggagt acaactacat cagccacaac gtctatatca    540
ccgccgacaa gcagaagaac ggcatcaagg ccaacttcaa gatccgccac aacatcgagg    600
acggcagcgt gcagctcgcc gaccactacc agcagaacac ccccatcggc gacggccccg    660
tgctgctgcc cgacaaccac tacctgagca cccagtccgc cctgagcaaa gaccccaacg    720
agaagcgcga tcacatggtc ctgctggagt tcgtgaccgc cgccgggatc actctcggca    780
tggacgagct gtacaagagg cctgctgcaa cgacgaaaaa ctacgctttt agtagcttaat   840 aatactagag ccaggcatca ataaaaacga aaggctcagt cgaaagactg ggcctttcgt    900
tttatctgtt gtttgtcggt gaacgctctc tactagagtc acactggctc accttcgggt    960
gggcctttct gcgtttata                                                 979
```

<210> SEQ ID NO 7
<211> LENGTH: 401
<212> TYPE: DNA
<213> ORGANISM: Rattus norvegicus

<400> SEQUENCE: 7

```
tagaaactat gaaacagttc cagggacaaa gataccaggt ccccaacaac tgcaactttc     60
tgggaaatga ggtggaaaat gctcagccaa ggaaaaagag ggccttaccc tctctgggac    120
aatgattgtg ctgtgaactg cttcatcagg ccatctggcc ccttgttaat aatctaatta    180
ccctaggtct aagtagagtt gttgacgtcc aatgagcgct ttctgcagac ttagcactag    240
gcaagtgttt ggaaattaca gcttcagccc ctctcgccat ctgcctacct accccctccta   300 gagcccttaa tgggccaaac ggcaaagtcc aggggggcaga gaggaggtgc tttggactat    360
aaagctagtg gagacccagt aactcccaac cctaagtgac c                        401
```

<210> SEQ ID NO 8
<211> LENGTH: 333
<212> TYPE: DNA
<213> ORGANISM: Artificial sequence
<220> FEATURE:
<223> OTHER INFORMATION: Synthetic construct

<400> SEQUENCE: 8

```
atggcgctgt ggatgcgcct gttaccgctg ttagcgctgc tggcactgtg ggggcctgat     60
ccggcggcag cttttgtgaa tcagcacctg tgcggtagtc atctggtcga agccctgtat    120
ctggtgtgcg gtgaacgtgg gttttttctat acgccgaaaa ctcgccggga ggccgaggac    180
ctgcaggttg gtcaggtaga actgggcggt ggtccaggcg ccggctcact gcagccgctg    240
gctctggagg gcagcttaca aaagcgtggc atcgttgaac aatgttgcac ctccatttgt    300
tctttatacc agttagaaaa ctactgtaac taa                                 333
```

<210> SEQ ID NO 9
<211> LENGTH: 27
<212> TYPE: DNA
<213> ORGANISM: Artificial sequence
<220> FEATURE:
<223> OTHER INFORMATION: Synthetic construct (5' to 3')

```
<400> SEQUENCE: 9
ttcgaaatcc tagaaactat gaaacag                                    27

<210> SEQ ID NO 10
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 10
ggatccggtc acttagggtt ggg                                        23

<210> SEQ ID NO 11
<211> LENGTH: 32
<212> TYPE: DNA
<213> ORGANISM: Artificial sequence
<220> FEATURE:
<223> OTHER INFORMATION: Synthetic construct (5' to 3')

<400> SEQUENCE: 11
ggtaccttct ttcgatggta aatgaaatag ga                              32

<210> SEQ ID NO 12
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 12
ggatccagtt gattgtatgc ttg                                        23

<210> SEQ ID NO 13
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 13
ctcgaggtga tagagattga cat                                        23

<210> SEQ ID NO 14
<211> LENGTH: 30
<212> TYPE: DNA
<213> ORGANISM: Artificial sequence
<220> FEATURE:
<223> OTHER INFORMATION: Synthetic construct (5' to 3')

<400> SEQUENCE: 14
tctagaaacg cagaaaggcc cacccgaagg                                 30

<210> SEQ ID NO 15
<211> LENGTH: 32
<212> TYPE: DNA
<213> ORGANISM: Artificial sequence
<220> FEATURE:
<223> OTHER INFORMATION: Synthetic construct (5' to 3')

<400> SEQUENCE: 15
ctcgagttct ttcgatggta aatgaaatag ga                              32

<210> SEQ ID NO 16
<211> LENGTH: 23
```

```
<212> TYPE: DNA
<213> ORGANISM: Artificial sequence
<220> FEATURE:
<223> OTHER INFORMATION: Synthetic construct (5' to 3')

<400> SEQUENCE: 16
tctagactat tcttcttcgt cct                                             23

<210> SEQ ID NO 17
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 17
tctagattat aaacgcagaa agg                                             23

<210> SEQ ID NO 18
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 18
ctcgagggat tcaaagagga gaa                                             23

<210> SEQ ID NO 19
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 19
tctagattat aaacgcagaa agg                                             23

<210> SEQ ID NO 20
<211> LENGTH: 1155
<212> TYPE: DNA
<213> ORGANISM: Saccharomyces cerevisiae

<400> SEQUENCE: 20
atgtccaaga gcaaaacttt cttatttacc tctgaatccg tcggtgaagg tcacccagac      60
aagatttgtg accaagtttc tgatgctatt ttggacgctt gtttagaaca agatccattc     120
tccaaggttg cctgtgaaac agctgccaaa actggtatga ttatggtttt cggtgaaatt     180
accaccaaag ctagacttga ctaccaacaa atagtaagag ataccatcaa gaagattggt     240
tatgacgatt ctgccaaggg tttcgactac aagacatgta atgttttagt agctatcgaa     300
caacaatctc cagatatcgc tcaaggtctg cactatgaaa agagcttaga agacttaggt     360
gctggtgacc aaggtataat gtttggttac gctacagacg aaactccaga agggttacca     420
ttgaccattc ttttggctca caattgaac atggctatgg cagatgctag aagagatggt     480
tctctcccat ggttgagacc agacacaaag actcaagtca ctgtcgaata cgaagacgac     540
aatggtagat gggttccaaa gaggatagat accgttgtta tttctgctca acatgctgat     600
gaaatttcca ccgctgactt gagaactcaa cttcaaaaag atattgttga aaaggtcata     660
ccaaaggata tgttagacga aaataccaaa tatttcatcc aaccatccgg tagattcgtc     720
atcggtggtc ctcaaggtga cgctggtttg accggtagaa agattattgt cgacgcttac     780
```

```
ggtggtgcct catccgtcgg tggtggtgcc ttctccggta aggactattc caaggtcgat      840
cgttccgctg cttacgctgc tagatgggtt gccaagtctc tagttgccgc tggtttgtgt      900
aagagagtcc aagtccaatt ttcatatgct attggtattg ctgaaccatt gtctttacat      960
gtggacacct atggtacagc tacaaaatca gatgacgaaa tcattgaaat tattaagaag     1020
aacttcgact tgagaccagg tgtgttagta aggaattag  atttggctag accaatttac     1080
ttaccaaccg cttcttatgg tcacttcact aatcaagagt actcatggga aaaaccaaag     1140
aaattggaat tttaa                                                      1155

<210> SEQ ID NO 21
<211> LENGTH: 1503
<212> TYPE: DNA
<213> ORGANISM: Saccharomyces cerevisiae

<400> SEQUENCE: 21
atgtctagat tagaaagatt gacctcatta aacgttgttg ctggttctga cttgagaaga      60
acctccatca ttggtaccat cggtccaaag accaacaacc cagaaacctt ggttgctttg     120
agaaaggctg gtttgaacat tgtccgtatg aacttctctc acggttctta cgaataccac     180
aagtctgtca ttgacaacgc cagaaagtcc gaagaattgt acccaggtag accattggcc     240
attgctttgg acaccaaggg tccagaaatc agaactggta ccaccaccaa cgatgttgac     300
tacccaatcc caccaaacca cgaaatgatc ttcaccaccg atgacaagta cgctaaggct     360
tgtgacgaca gatcatgta  cgttgactac aagaacatca ccaaggtcat ctccgctggt     420
agaatcatct acgttgatga tggtgttttg tctttccaag ttttggaagt cgttgacgac     480
aagactttga aggtcaaggc tttgaacgcc ggtaagatct gttcccacaa gggtgtcaac     540
ttaccaggta ccgatgtcga tttgccagct tgtctgaaa  aggacaagga agatttgaga     600
ttcggtgtca agaacggtgt ccacatggtc ttcgcttctt tcatcagaac cgccaacgat     660
gttttgacca tcagagaagt cttgggtgaa caaggtaagg acgtcaagat cattgtcaag     720
attgaaaacc aacaaggtgt taacaacttc gacgaaatct gaaggtcac  tgacggtgtt     780 atggttgcca gaggtgactt gggtattgaa atcccagccc agaagtcttg ggctgtccaa     840
aagaaattga ttgctaagtc taacttggct ggtaagccag ttatctgtgc tacccaaatg     900
ttggaatcca tgacttacaa cccaagacca ccagagctg  aagtttccga tgtcggtaac     960
gctatcttgg atggtgctga ctgtgttatg ttgtctggtg aaaccgccaa gggtaactac     1020
ccaatcaacg ccgttaccac tatggctgaa accgctgtca ttgctgaaca agctatcgct     1080
tacttgccaa actacgatga catgagaaac tgtactccaa agccaacctc caccaccgaa     1140
accgtcgctg cctccgctgt cgctgctgtt ttcgaacaaa aggccaaggc tatcattgtc     1200
ttgtccactt ccggtaccac cccaagattg gtttccaagt cagaccaaa  ctgtccaatc     1260 atcttggtta ccagatgccc aagagctgct agattctctc acttgtacag aggtgtcttc     1320
ccattcgttt tcgaaaagga acctgtctct gactggactg atgatgttga agcccgtatc     1380
aacttcggta ttgaaaaggc taaggaattc ggtatcttga agaagggtga cacttacgtt     1440
tccatccaag gtttcaaggc cggtgctggt cactccaaca ctttgcaagt ctctaccgtt     1500
taa                                                                  1503

<210> SEQ ID NO 22
<211> LENGTH: 765
<212> TYPE: DNA
<213> ORGANISM: Saccharomyces cerevisiae
```

<400> SEQUENCE: 22

```
atgagtatcg ctgaattcgc ttacaaggaa aaaccagaaa ctttggtttt attcgatgtt      60
gatggtacct tgacaccagc cagattaact gtttctgaag aagttagaaa aactttggcc     120
aagttgagaa acaagtgctg cattggtttt gtcggtggtt ctgacttaag caagcaatta     180
gaacagttag gcccaaacgt tttagatgaa tttgactatt cttctctga aatggtttg      240
accgcctaca gattaggtaa ggaattagct tctcaatcct tcatcaactg gctcggtgag     300
gaaaaataca ataaattggc cgtcttcatt ttgagatatc tatctgaaat tgacttgcca     360
aagagaagag gtactttctt ggaatttaga atggtatga tcaacgtttc cccaattggt      420
agaaatgctt ctactgagga aagaaacgaa ttcgaaagat acgataagga acaccaaatc     480
agagccaagt tcgttgaagc tttgaaaaag gaattcccag actacggttt gactttctcc     540
attggtggcc aaatctcttt cgacgttttc cccgctggtt gggataagac ctactgtttg     600
caacacgttg aaaagatgg tttcaaggaa attcatttct tggtgacaa gactatggtc      660
ggtggtaacg attacgaaat ttttgtcgat gaaagaacca tcggacattc agtacaatcc     720
cctgatgaca ccgtcaaaat tttgactgaa ctattcaact tatag                      765
```

<210> SEQ ID NO 23
<211> LENGTH: 1005
<212> TYPE: DNA
<213> ORGANISM: Saccharomyces cerevisiae

<400> SEQUENCE: 23

```
atgttgtcaa gagtagctaa acgtgcgttt tcctctacag ttgccaaccc ttataaagtg      60
actgttttgg gtgcaggcgg tggtattgga caaccattgt ctttgcttct aaagcttaac     120
cataaagtca cggacttaag actgtacgac ctaaagggcg caaaggtgt tgccaccgat      180
ttgtctcata ttccaacaaa ctccgtggtc aaggggttta ctccagaaga gccagacgga     240
ttgaacaacg ctttaaagga cacagacatg gttttaattc ctgctggtgt gcccagaaag     300
cctggtatga cacgtgatga cttgttcgcc atcaacgcaa gcatcgttcg cgatttggca     360
gcagcaaccg ccgaatccgc tcccaatgct gccattctgg tcatttccaa cccagtcaat     420
tctaccgttc caattgtcgc ccaagtcttg aaaaacaagg gtgtttacaa cccaagaaa      480
ttgttcggtg tgactacctt ggactctatt agagccgcca gattcatctc agaagtcgag     540
aacaccgatc caactcagga aagggttaac gtcatcggtg acattctgg tattaccatc      600
atcccattga tttcgcaaac aaaccataag ttgatgtctg atgacaagag acacgaattg     660
attcacagaa tacagtttgg tggtgacgaa gtcgtcaaag caagaatgg tgctggctct      720
gctacgttgt caatggccca tgctggtgct aaattcgcta acgctgtttt gtccggtttc     780
aaaggcgaaa gagacgtcat cgagccttcc ttcgtggact ctcccttgtt caaatccgaa     840
ggcatcgaat tctttgcatc tccggtcact ttgggcccag atggtattga aaagatccat     900
ccaataggtg agttatcttc agaagaagaa gaaatgctac aaaaatgtaa agaaaccttg     960
aagaagaata tcgaaagggg tgtcaacttt gttgctagta aatag                    1005
```

<210> SEQ ID NO 24
<211> LENGTH: 1458
<212> TYPE: DNA
<213> ORGANISM: Saccharomyces cerevisiae

<400> SEQUENCE: 24

```
atggttcatt taggtccaaa gaaaccacag gctagaaagg gttccatggc tgatgtgccc    60
aaggaattga tggatgaaat tcatcagttg aagatatgt ttacagttga cagcgagacc   120
```

```
atggttcatt taggtccaaa gaaaccacag gctagaaagg gttccatggc tgatgtgccc    60
aaggaattga tggatgaaat tcatcagttg aagatatgt  ttacagttga cagcgagacc   120
ttgagaaagg ttgttaagca ctttatcgac gaattgaata aaggtttgac aaagaaggga   180
ggtaacattc caatgattcc cggttgggtc atggaattcc caacaggtaa agaatctggt   240
aactatttgg ccattgattt gggtggtact aacttaagag tcgtgttggt caagttgagc   300
ggtaaccata cctttgacac cactcaatcc aagtataaac taccacatga catgagaacc   360
actaagcacc aagaggagtt atggtccttt attgccgact cttgaagga ctttatggtc    420 gagcaagaat tgctaaacac caaggacacc ttaccattag gtttcacctt ctcgtaccca   480
gcttcccaaa acaagattaa cgaaggtatt ttgcaaagat ggaccaaggg tttcgatatt   540
ccaaatgtcg aaggccacga tgtcgtccca ttgctacaaa acgaaatttc caagagagag   600
ttgcctattg aaattgtagc attgattaat gatactgttg gtactttaat tgcctcatac   660
tacactgacc cagagactaa gatgggtgtg attttcggta ctggtgtcaa cggtgctttc   720
tatgatgttg tttccgatat cgaaaagttg gagggcaaat tagcagacga tattccaagt   780
aactctccaa tggctatcaa ttgtgaatat ggttccttcg ataatgaaca tttggtcttg   840
ccaagaacca agtacgatgt tgctgtcgac gaacaatctc caagacctgg tcaacaagct   900
tttgaaaaga tgacctccgg ttactacttg ggtgaattgt tgcgtctagt gttacttgaa   960
ttaaacgaga agggcttgat gttgaaggat caagatctaa gcaagttgaa acaaccatac  1020
atcatggata cctcctaccc agcaagaatc gaggatgatc catttgaaaa cttggaagat  1080
actgatgaca tcttccaaaa ggactttggt gtcaagacca ctctgccaga acgtaagttg  1140
attagaagac tttgtgaatt gatcggtacc agagctgcta gattagctgt ttgtggtatt  1200
gccgctattt gccaaaagag aggttacaag actggtcaca ttgccgctga cggttctgtc  1260
tataacaaat acccaggttt caaggaagcc gccgctaagg gtttgagaga tatctatgga  1320
tggactggtg acgcaagcaa agatccaatt acgattgttc cagctgagga tggttcaggt  1380
gcaggtgctg ctgttattgc tgcattgtcc gaaaaaagaa ttgccgaagg taagtctctt  1440
ggtatcattg gcgcttaa                                                1458

<210> SEQ ID NO 25
<211> LENGTH: 468
<212> TYPE: DNA
<213> ORGANISM: Hordeum vulgare

<400> SEQUENCE: 25
atgctcgtgt accaggacaa gctttccggc gatgaactcc tgtcggattc cttcccgtac    60
agggagctgg agaacggtgt gctctgggaa gtcgatggcc attgggtcgt tcaaggagca   120
gttgatgtgg acattggtgc caacccctct gctgagggtg tggtgagga tgagggtgtc    180 gatgaccagg ccgtgaaggt ggttgacatt gttgacacct tccgtcttca ggagcaacct   240
gcttttgaca agaagcagtt tattgcttac atcaagcgct acatcaagaa cctcactgcc   300
aagcttgaag gtgaggagct agatgctttc aagaagaacg ttgagtctgc cacgaagtat   360
cttcttagca agctcaagga ccttcagttc tttgtgggcg agagcatgca tgatgatggc   420
agcgtggtgt ttaagcttga ttgcctacta cagggaggga gctgctga               468

<210> SEQ ID NO 26
<211> LENGTH: 6438
<212> TYPE: DNA
<213> ORGANISM: Saccharomyces cerevisiae
```

<400> SEQUENCE: 26

```
atgccagtgt tgaaatcaga caatttcgat ccattggaag aagcttacga aggtgggaca    60
attcaaaact ataacgatga acaccatctt cataaatctt gggcaaatgt gattccggac   120
aaacgaggac tttacgaccc tgattatgaa catgacgctt gtggtgtcgg tttcgtagca   180
aataagcatg gtgaacagtc tcacaagatt gttactgacg ctagatatct tttagtgaat   240
atgacacatc gtggtgccgt ctcatctgat gggaacggtg acggtgccgg tattctgcta   300
ggtattcctc acgaatttat gaaaagagaa ttcaagttag atcttgatct agacatacct   360
gagatgggca atacgccgt aggtaacgtc ttcttcaaga agaacgaaaa aaataacaag    420
aaaaatttaa ttaagtgtca gaagattttc gaggatttag ctgcatcctt caacttatcc   480
gtattaggtt ggagaaacgt ccccgtagat tctactattt taggagacgt tgcattatct   540
cgtgaaccta ctattctaca gccattattg gttccattgt atgatgaaaa acaaccggag   600
tttaatgaaa ctaaatttag aactcaattg tatcttttaa ggaaggaggc ctctcttcaa   660
ataggactgg aaaactggtt ctatgtttgt tccctaaaca ataccaccat tgtttacaag   720
ggtcaattga cgccagctca agtgtataac tactatcccg acttgactaa tgcgcatttc   780
aaatcccaca tggcgttggt ccattcaaga ttttccacta atactttccc ctcttgggat   840
agagctcaac ctttacgttg gctagctcat aatggtgaaa ttaacacctt aagaggtaac   900
aagaattgga tgcgctccag agaaggtgtg atgaattcag caactttcaa agatgagtta   960
gacaaactat acccaattat cgaagaaggt ggttctgatt cagctgcatt ggataacgtt  1020
ttagaactat tgactattaa tggcacatta tctctacctg aagctgttat gatgatggtt  1080
cctgaagcgt atcataagga tatggattct gacctaaaag catggtacga ctgggctgca  1140
tgtctgatgg aaccttggga tggtccagct ttgttaactt tcactgatgg acgttactgt  1200
ggtgctatat tggatagaaa tggtttaaga ccttgtcgtt attacatcac tagtgatgac  1260
agagttatct gtgcttcaga ggtaggtgtc attcctatcg aaaattcatt ggttgttcaa  1320
aaaggtaaac tgaagccagg tgatttattc ctagtggata ctcaattggg tgaaatggtc  1380
gatactaaaa agttaaaatc tcaaatctca aaaagacaag attttaagtc ttggttatcc  1440
aaagtcatca agttagacga cttgttatca aaaaccgcta atttggttcc taaagaattt  1500
atatcacagg attcattgtc tttgaaagtt caaagtgacc cacgtctatt ggccaatggt  1560
tataccttcg aacaagtcac atttctgtta actccaatgg ctttaacagg taaagaagct  1620
ttaggttcga tgggtaacga tgcgccactg gcttgtttaa atgaaaatcc tgtcttactt  1680
tatgattatt tcagacaatt gtttgctcaa gtgaccaatc ctccaattga cccaattcgt  1740
gaagcaaatg ttatgtcgtt agaatgttat gtcggacctc aaggcaacct tttggaaatg  1800
cattcatctc aatgtgatcg tttattattg aaatctccta ttttgcattg gaatgagttc  1860
caagctttga aaaacattga agctgcttac ccatcatggt ctgtagcaga aattgatatc  1920
acattcgaca agagtgaggg tctattgggc tataccgaca caattgataa aatcactaag  1980
ttagcgagcg aagcaattga tgatggtaaa aagatcttaa taattactga caggaaaatg  2040
ggtgccaacc gtgtttccat ctcctctttg attgcaattt catgtattca tcatcaccta  2100
atcagaaaca agcagcgttc ccaagttgct ttgatttggg aaacaggtga agccagagaa  2160
attcaccatt tctgtgtcct actaggttat ggttgtgatg gtgtttatcc atacttagcc  2220
atggaaactt tggtcagaat gaatagagaa ggtctacttc gtaatgtcaa caatgacaat  2280
```

```
                                    -continued
gatacacttg aggaagggca aatactagaa aattacaagc acgctattga tgcaggtatc    2340
ttgaaggtta tgtctaaaat gggtatctcc actctagcat cctacaaagg tgctcaaatt    2400
tttgaagccc taggtttaga taactctatt gttgatttgt gtttcacagg tacttcttcc    2460
agaattagag gtgtaacttt cgagtatttg gctcaagatg cctttctttt acatgagcgt    2520
ggttatccat ccagacaaac cattagtaaa tctgttaact taccagaaag tggtgaatac    2580
cactttaggg atggtggtta caaacacgtc aacgaaccaa ccgcaattgc ttcgttacaa    2640
gatactgtca gaaacaaaaa tgatgtctct tggcaattat atgtaaagaa ggaaatggaa    2700
gcaattagag actgtacact aagaggactg ttagaattag atttttgaaaa ttctgtcagt    2760 atccctctag aacaagttga accatggact gaaattgcca gaagatttgc gtcaggtgca    2820
atgtcttatg gttctatttc tatggaagct cactctacat tggctattgc catgaatcgt    2880 ttagggggcca atccaattg tggtgaaggt ggtgaagacg cagaacgttc tgctgttcaa    2940
gaaaacggtg atactatgag atctgctatc aaacaagttg cttccgctag attcggtgta    3000
acttcatact acttgtcaga tgctgatgaa atccaaatta gattgctca gggtgctaag    3060 ccgggtgaag gtggtgaact accagcccac aaagtgtcta aggatatcgc aaaaaccagg    3120
cactccaccc ctaatgttgg gttaatctct cctcctcctc atcacgatat ttattccatt    3180
gaagatttga acaactgat ttatgatttg aaatgtgcta atccaagagc gggaatttct    3240
gtaaagttgg tttccgaagt tggtgttggt attgttgcct ctggtgtagc taaggctaaa    3300
gccgatcata tcttagtttc tggtcatgat ggtggtacag gtgctgcaag atggacgagt    3360
gtcaaatatg cgggttttgcc atgggaatta ggtctagctg aaactcacca gactttagtc    3420
ttgaatgatt taagacgtaa tgttgttgtc caaaccgatg gtcaattgag aactgggttt    3480
gatattgctg ttgcagtttt attaggggca gaatctttta ccttggcaac agttccatta    3540
attgctatgg gttgtgttat gttaagaaga tgtcacttga actcttgtgc tgttggtatt    3600
gccacacaag atccatattt gagaagtaag tttaagggtc agcccgaaca tgttatcaac    3660
ttcttctatt acttgatcca agatttaaga caaatcatgg ccaagttagg attccgtacc    3720
attgacgaaa tggtgggtca ttctgaaaaa ttaaagaaaa gggacgacgt aaatgccaaa    3780 gccataaaata tcgatttatc tcctattttg accccagcac atgttattcg tccaggtgtt    3840
ccaaccaagt tcactaagaa acaagaccac aaactccaca cccgtctaga taataagtta    3900
atcgatgagg ctgaagttac tttggatcgt ggcttaccag tgaatattga cgcctctata    3960
atcaatactg atcgtgcact cggttctact ttatcttaca gagtctcgaa gaaatttggt    4020
gaagatggtt tgccaaagga caccgttgtc gttaacatag aaggttcagc gggtcaatct    4080
tttggtgctt tcctagcttc tggtatcact tttatcttga atggtgatgc taatgattat    4140
gttggtaaag gtttatccgg tggtattatt gtcattaaac caccaaagga ttctaaattc    4200
aagagtgatg aaaatgtaat tgttggtaac acttgtttct atggtgctac ttctggtact    4260
gcattcattt caggtagtgc cggtgagcgt ttcggtgtca gaaactctgg tgccaccatc    4320
gttgttgaga gaattaaggg taacaatgcc tttgagtata tgactggtgg tcgtgccatt    4380
gtcttatcac aaatggaatc cctaaacgcc ttctctggtg ctactggtgg tattgcatac    4440
tgtttaactt ccgattacga cgattttgtt ggaaagatta acaaagatac tgttgagtta    4500
gaatcattat gtgacccggt cgagattgcg tttgttaaga atttgatcca ggagcattgg    4560
aactacacac aatctgatct agcagccagg attctcggta atttcaacca ttatttgaaa    4620
gatttcgtta aagtcattcc aactgattat aagaaagttt tgttgaagga gaaagcagaa    4680
```

-continued

```
gctgccaagg caaaggctaa ggcaacttca gaatacttaa agaagtttag atcgaaccaa    4740
gaagttgatg acgaagtcaa tactctattg attgctaatc aaaaagctaa agagcaagaa    4800
aaaaagaaga gtattactat ttcaaataag gccactttga aggagcctaa ggttgttgat    4860
ttagaagatg cagttccaga ttccaaacag ctagagaaga atagcgaaag gattgaaaaa    4920
acacgtggtt ttatgatcca caaacgtcgt catgagacac acagagatcc aagaaccaga    4980
gttaatgact ggaaagaatt tactaaccct attaccaaga aggatgccaa atatcaaact    5040
gcgagatgta tggattgtgg tacaccattc tgtttatctg ataccggttg tccctatct     5100 aacattatcc ccaagtttaa tgaattgtta ttcaagaacc aatggaagtt ggcactggac    5160
aaattgctag agacaaacaa tttcccagaa ttcactggaa gagtatgtcc agcaccctgt    5220
gagggagctt gtacactagg tattattgaa gacccagtcg gcataaaatc ggttgaaaga    5280
attatcattg acaatgcttt caaggaagga tggattaagc cttgtccacc aagtacacgc    5340
actggcttta cagtgggtgt cattggttct ggtccagcag gtttagcgtg tgctgatatg    5400
ttgaaccgtg ccggacatac ggtcactgtt tatgaaagat ccgaccgttg tggtgggtta    5460
ttgatgtatg gtattccaaa catgaagttg ataaggcta tagtgcaacg tcgtattgat    5520
ctattgagtg ccgaaggtat tgactttgtt accaacaccg aaattggtaa aaccataagc    5580
atggatgagc taaagaacaa gcacaatgca gtagtgtatg ctatcggttc taccattcca    5640
cgtgacttac ctattaaggg tcgtgaattg aagaatattg attttgccat gcagttgttg    5700
gaatctaaca caaaagcttt attgaacaaa gatctggaaa tcattcgtga aaagatccaa    5760
ggtaagaaag taattgttgt cggtggtggt gacacaggta acgattgttt aggtacatct    5820 gtaagcacg gtgcagcatc agttttgaat ttcgaattgt tgcctgagcc accagtggaa    5880
cgtgccaaag acaatccatg gcctcaatgg ccgcgtgtca tgagagtgga ctacggtcat    5940
gctgaagtga aagagcatta tggtagagac cctcgtgaat actgcatctt gtccaaggaa    6000
tttatcggta acgatgaggg tgaagtcact gccatcagaa ctgtgcgcgt agaatggaag    6060
aagtcacaaa gtggcgtatg gcaaatggta gaaattccca acagtgaaga gatcttttgaa   6120 gccgatatca ttttgttgtc tatgggtttc gtgggtcctg aattgatcaa tggcaacgat    6180
aacgaagtta agaagacaag acgtggtacg attgccacac tcgacgactc ctcatactct    6240
attgatggag gaaagacttt tgcatgtggt gactgtagaa gagggcaatc tttgattgtc    6300
tgggccatcc aagaaggtag aaaatgtgct gcctctgtcg ataagttcct aatggacggc    6360
actacgtatc taccaagtaa tggtggtatc gttcaacgtg attacaaact attgaaagaa    6420
ttagctagtc aagtctaa                                                  6438
```

<210> SEQ ID NO 27
<211> LENGTH: 2409
<212> TYPE: DNA
<213> ORGANISM: Saccharomyces cerevisiae

<400> SEQUENCE: 27

```
atgctcaaca ttctcgtttt aggaaacggt gcaagagaac acgttcttgt caccaagctg     60
gctcagtcac ccaccgtggg taagatctat gtcgctccag gtaatggagg accgcaacc    120 atggatcctt cgcgtgtgat aaactgggat attacgccag atgtcgccaa ttttgctcgt    180
ttgcagtcga tggctgtgga acataagatc aacttggtcg ttcctggtcc agaattacct    240
ctagtcaacg gcatcaccct cgtgttccat agcgttggta ttcccgtttt tggaccttcc    300
```

```
gtcaaagccg ctcagttgga agcttccaag gctttctcca agagattat gtcaaaacac     360
aatattccaa ccgcgtctta tgatgtcttc actaatccag aagaagccat ttcattcttg     420
caagctcata ctgacaaagc ttttgtcatc aaggccgacg ggatcgctgc tgggaaaggt     480
gttattatcc catctagcat cgacgagtcc gtccaagcta tcaaggacat aatggtcacc     540
aagcaattcg gtgaagaagc gggcaagcag gttgtgatag aacaattctt ggaaggtgat     600
gaaatctctc tactcaccat tgttgacggg tactctcact tcaatctccc cgtcgcacaa     660
gatcacaaga ggatctttga tggcgacaag ggcttgaaca ccggtgggat gggtgcctat     720
gcccccgctc ctgtggccac accatctttg ttgaagacca tagattcaca gattgtgaag     780
cctacgattg atgggatgag acgtgatggt atgccctttg ttggtgtgct gttcaccggg     840
atgatttttgg tgaaggattc taagacaaat caacttgttc cgaagtgtt agaatataat     900
gtcagattcg gtgacccaga gacacaggct gttttgagtt tacttgatga tcaaaccgat     960
ttggcgcaag tgttttttggc tgctgctgaa catcgtttgg attccgtaaa cataggaatc    1020
gatgacacaa gatctgccgt tactgtcgta gtggctgcag tggttatcc tgaatcatac    1080
gccaaaggtg acaaaattac cttggatacc gataaattac ctccacatac acaaatcttc    1140
caagcaggta ccaaatacga ttccgccacc gattctttat tgaccaatgg tggtagagtt    1200
ctttctgtga cctccactgc tcaggacttg agaacagcag tagatacagt atatgaagcc    1260
gtcaaatgcg tccatttcca aaattcttac tacagaaagg acatcgcata ccgtgcgttc    1320
caaaactcag aatcatcaaa agttgccatc acatacgcag actcaggtgt ctctgttgat    1380
aatggtaaca atctcgtaca aactatcaaa gaaatggtca gatccacaag aaggccaggt    1440
gcagactctg atattggtgg ttttggtggt ttattcgatt tggctcaagc aggtttccgt    1500
caaaacgaag ataccttact agtaggtgct acagatggtg tcggtactaa attaatcatt    1560
gcccaagaga ccgggattca taatactgtc ggtattgacc tggtggccat gaatgttaac    1620
gatttggtgg tacaaggtgc tgagcctcta ttcttttttgg actactttgc cactggtgct    1680
cttgacattc aagttgcctc tgattttgtg tccggtgttg ctaatggttg tattcaaagt    1740
ggttgtgctc ttgtgggtgg tgaaacttcg gaaatgcccg gtatgtatcc acccggccac    1800
tacgatacta atggtaccgc tgttggtgct gtattaagac aagatatctt gcccaagata    1860
aatgaaatgg ccgcaggaga tgttcttctg ggtctcgcct ctagcggtgt tcattctaat    1920
ggtttctctt tggttagaaa aattattcaa catgtagcat taccatggga cgctccatgt    1980
ccatgggatg aatctaagac gttaggtgaa ggtattcttg aaccaacaaa aatttacgtc    2040
aagcaattat tgccatcaat tagacaaaga ctactactag gtttagctca tataacaggt    2100
ggtggtttag tagagaatat cccaagagct attccagacc acctacaggc ccgcgttgat    2160
atgtcaacct gggaagtacc ccgtgtcttc aaatggtttg gtcaagcagg taatgttcca    2220
cacgatgaca ttttaagaac cttcaacatg ggtgttggta tggttttgat tgtcaagaga    2280
gaaaacgtca aggctgtttg tgattcattg actgaagaag gtgaaattat ttgggagctt    2340
ggttctttgc aagaaagacc aaaggatgct cccggttgtg tgattgaaaa cggaactaag    2400
ctttactaa                                                            2409
```

<210> SEQ ID NO 28
<211> LENGTH: 13047
<212> TYPE: DNA
<213> ORGANISM: Mus musculus

<400> SEQUENCE: 28

```
cggttcacta gaggagggaa gaagtctaca aggacccatc aatttcctgc ctgcctgcag      60
caaggacaga cggcatgagc actgcgggaa agtaaggaa aagatctcac tgttggaaat     120
gtattctcag taatacgtgg agagatgcag agtcctacct tagaaataac aggctctgat    180
ctgctgtagt gcagaaggtg tcctgggtga gcacagcttg acctgctact aaatatcttt    240
aacaagaggg catagaacct gggtttgtga aagtctttat tccctcactt cctctgcagg    300
acagggaact tattccaagt cagtggtggc tgctttgcaa acagaaagtt tttaaaaagg    360
tcttttactg aaagtctgta tttatcaata atgtgttatt ctttctggtc atattttgtt    420
atgaacatag aaaagttaaa tctggcaaga gtttcatagg aggaatttga ttcagggagc    480
ttagtactgt tcctgtagcc attaggtaac gtttctggtg agagatggac tgatttgaaa    540
gcattagagt cattcacagt aagattatgt taccatgtaa attgtgattt gaagggccca    600
ttattgcaca actcacggat ttctacaaaa atcctataaa cagtctctct cctgttttaaa   660 aaaaaatcat ccagatttta tggaaaatta atttgaataa aaatggaact gattgttagt    720
attaagaata cacacatatg gtactgagtt ttccacaaaa atcacactca tttgttcagc    780
gtttacatgg taccgcaatg atggtgaaca gccaatcagt ataattaatt atctatcgct    840
taattatata agcctatgtt tctgttggca cagaggctat tttaggagtg ggtcaagagt    900
ccaacaactg acagtgagaa ctgggtgtcc gacgtcgcag aggtttctgc acgcactgtg    960
tgacaaaatt cttcattttt atttcaattc acttcacact ggttatgttt agggtggcat   1020
attacatttc aaagaaaaag cagttaggaa aaaaagttaa actgaaattt ctagctgaaa   1080
aagtaaaaaa aaaaaaaaaa gtaagttcat acagcaagaa tgtaaaccca ccacatccat   1140
caaacagcaa tcgagggagg ggacagagaa agcagtctga ggtacagagg tcaataacag   1200
tgctgtgatg atagtcagtc tatgcttata cttcctagag cagcaaaatc ataatgtagc   1260
caggtatggt agaatatctc tgaaatcttg ggaataggaa ggcccctagc ttaaggccag   1320
cctgggctgc ttattagaat ttttgtctca gaagtcccac ccctgggggt taactctgtg   1380
atagaggact tgcctagagt gcacaaagtt ctgggtactg tcctcggtgc ctgaaaaata   1440
aataattata atttagaatt aaatatatgc ccaacaattg cacagaaaca accttttttgg  1500 ggacagtaca ggtgacatcc agaaagcaaa ccaacaagca agcagtcaaa acatggggca   1560
gcgtagcttg acagcacccg tgtcacttta acttggtata ctacacttac ttgtgttttc   1620
ccgaccttgg gctaagctgt cacacatttt tttaaaggct ttttaactct ttgtaaatca   1680
gaactgtctg tctctatgta acacttactg ggtgacatag acggggacag atgatatata   1740
tatatatata tatatatata tatatatatg tgtgtgtgtg tgtgtatata tatatatata   1800
tatatatata tatatatata tacatacata catatacata tacacacaca tatatgtatg   1860
tatgtatatg tgtgcatgta tatgtatatg tatatgtgta tgtgtatgtg tatgtgtgtg   1920
tgtgtgtgtg tgtgtgtgtg tgtgtgtgta tgtgtatgtg tatatgtata tgtatatgta   1980
tatgtatatg tatatgtata tgtataatgt atatgtatat gtacatgaat gaaaggatgc   2040
aatcgcagtg atgtcattgg agctgaagta acccttcgct ttccaggtga tcaaatgcaa   2100
agctgcggtg ctatgggagc ttcacaaacc cttcaccatc gaggacatag aagtcgcacc   2160
ccccaaggcc catgaagttc gaattaaggt gactgccctt ttcaacttct gcaaagttag   2220
gttggaaaaa ctcgaaaagt actccatagc cacatccaga aatccgttaa tagccccttt   2280
catgtgctta attaatttgc tgctatcaat atcaaatgtc caaagtttga agtgactaga   2340
```

```
aagtatgttt aacctaatct cagaattttc tttagatgct tatgtgttta tgaagtgcta    2400
aaacatcttg agtccaaaac caactcatgt tgggtaatgt cttggtgcta atgtttgatt    2460
tctatttgca taaagcagca tgcattttca tatattccat aaaacacatt ttcagagcca    2520
cctactctac aggattgata attgagccat ttaattggga aaaggtaaac ggaaacactg    2580
gagaatcttg gagataaatg aactctttgg aatttggaag cagtaaggat tgttaggaag    2640
cccctcagaa gcacgactgc agacgaatag gcttgtgaaa cctccacaat cacaaacttg    2700
gttaactgga ctttaccttt aatccacaga tggtggccac tggtgtctgc cgctcagacg    2760
atcacgtggt tagtggaacc ctggtcacac ctcttcctgc agttttaggc catgagggag    2820
caggcattgt tgagagcgtt ggagaagggg tgacttgtgt gaaccaggt acagaattca     2880 ccctcagggc ttgtgtttcg gttctgatct caagagcatc cctcccaaga gaggaagttg    2940
aggaagtggg agatgaaaag ccaggcaata aaggcttcc tctgcccctt cctcccggca    3000
tgcctcagtc gtgctacatc caagcaagtc ttttctcttt caacatctgt ttatctccta    3060
catgtcaggc atcaagccag aggctcctat atgaagatct ggaagcacgg tgcccgtaag    3120
ggtgtgcagt ttataatctg ctaacttcta cttttattgtc cctgagcgct gtggactttc    3180
aaaacccaga cagaccttaa aaagtatccg aggcggaaa tgcaggtcca ggttctgaga     3240
tacacggcag ctgttctgtg ctgaacgcag agacgtgaag gcttgcccta ctcgcaggac    3300
gcccaccata gttttaacca cacactggga caacatgatg gcttcctctt ttcctgtatg    3360
ctccttcttt atgaatatag ataaaataaa atgtaagagg gaatataagg gaaaatcata    3420
gccaaaggcc ttcaaaccca cagaccttct tatcattaat tgtggctgta ggtggtaggt    3480
cacacagtat ttattgcgtt acacatggct ccactttata tgttttttaag gtaaagggtg    3540 agcaaaacat aaaatttccg tgataccatc ccacattaat tttatctatg aaatataatg    3600
accaaacctt ttttttttggt ccaataacat aggtagcata catgatttaa aaacaaaaat    3660
tatgttcatc ttcaaaaaga tcgctttagt caatagagtc agacttctct tctaaatgac    3720
taagctgtaa gcaaaaaata ggaaaagaac taatctggtt tgagttaagc ttgtattatt    3780
tcttttattc agaaaagaac aaaacaacaa caacaaacct agcagcaaaa tgacaccttt    3840
actcttcagg ttgcttcttc tatggcagaa aaatcaataa ttcataaata attatcttta    3900
aaaaacaaaa gttcttgtt atttcccaga gaaagtattt aactcattaa gaactgagat     3960
ttccaaagca atttgtggct tgtcatgttt ttattatgct tcctcaaaaa ataactaaga    4020
ttttttaagc ctttatttca tagtaggaga agcacaatca ccttaaaaag ccaaaactgg    4080
accacgaaga aatgataacg tggctcaggg cataccatgc tcttatagag cacccaactg    4140
ggttactcac aaccacttgt aactccagct cctggggacc caacacccctt tgctggcttc   4200 caagggcaca catacagaga tggcacacac acacaggtac tctcacatgc acacaaaag    4260 aaaaaaacca acaccaacaa caaagtctta aacaataaaa gggcaaaagc taactatcaa    4320
gattcccact ttaatttgat ttcatgatca agtttaattt gttttatttt tactataaaa    4380
tattgcctgt atagtgtttc tttaatctta cttttattga aactatcata tcagttctcg    4440
ccaaaatcta acaggaagat agcaactcat ttgcagagaa agtgtatatt tcttcttagc    4500
agcaagcata tccaaggttt gattaggata tgtacaaagc tcctaagaga aactgaggca    4560
cacaacaaag tttaactgct gacgggtgga aatggctggt ttcggctcat ttttctctcc    4620
cgggaatctt caggcgcttt aaatgcgaat gactaattag actgacatag cctgggtgag    4680
gcctcatctc ctggagactt ttcaaagaca caatgtctct aataagcttc aagttgttgc    4740
```

```
tttattgatt tctggacaga catttaagtc attttgtttt tcttcatcca ggtgataaag    4800
tcattccact cttttcccct cagtgtggag aatgcaggat ttgcaagcac ccggaaagca    4860
acttttgtag ccgaagcgag tacgtttctt attgtcttct tgcacagttg ggtgggcaca    4920
ctgctttgtt ctgtctcatg tcctttgtat gcctgtgttt caccaaccag tctgctaatg    4980
cctcggggga ctttgcgcga aggcaccagc aggttctcct gcaagggaaa gcagatccac    5040
aactttatca gcaccagcac cttctcccag tacaccgtgg tagatgatat agcagtggcc    5100
aaaatcgatg gagcttcacc actggacaaa gtctgcctca tcggctgtgg gttctcaact    5160
ggctatggct ctgccgtcaa agtcgccaag gtaggatgga cagtgggcca tggaacaagc    5220
taagtgcata ttattggtac ctaaagggaa gacatggctc ctgggcgggc atcagagtat    5280
ttttgtagaa gtgaaataag cctctccagc cccagtgaga attcactcca cacacttgag    5340
agaagcaagg gaaagctcta taatagtgtg tgtctagttc tagctcttgc ccaaagagaa    5400
accagcgtct aacagaaatt atttgaagtt tgtttaggtc ttgggctgta acattctaca    5460
tatgccattg tctgcagatc tctgttatgt cccagctgca agactcactg agcaatgaaa    5520
tacattttaa ggagacagaa actggaaagc ttgactatat tggacaaatg ggagatttta    5580
taaagtggag atgccatcac tgttatttct aaagcaagcc acaatgggga tatttgtact    5640
gcagagatag tgccacaagt gtgcgttagt ttgttttttaa gtagaccaac attgttacct    5700
agagccgtcc tgccttccag gtagaatttt ctagataaga aaaccaaggc ttttaatagc    5760
agagtagtac tccattgtgt agatgtacca cattttctgt atctatccat tcctctgttg    5820
aaagacatct gggttctttc cagcttctgg ctattataaa taaggctgtt atgaacatag    5880
tggagcatgt gtccttgtta tatgttggag catcttctgt gtatatgccc aggagtatat    5940
gctgagtcct catgtcaaat ttctgaggaa ccaacagact gatttccaga gtggttgtaa    6000
tcctaccaac aatggaggaa tgtgcctctt tctccacatc ctcaccagca tctgctgaaa    6060
ttcttaggca aatggatgga actagaaaat atcatcctga atgaggtaac ccaatcacaa    6120
aagaacacac atagtatgca ttcactaata agtggggata ttagccgcaa agcatggaat    6180
actcaagata caattcacag atcacataaa gctcaagaag aaggagacct aagtgtgggt    6240
ccttcttaga aagggaaaca aaagactgtt ggaagccaat atagagatga agcataaagc    6300
agaggctgaa ggaaggtcat ccagagaatt cactccacac atgccccact ggggatcca    6360 tcccaaatac agtcaccaaa gccagacact attgtagatg ccaagaagtg catgctgaca    6420
ggagcatgat acagctgtct cctgagaggc cctgccagac ccttacaaat acagatgcag    6480
atgctcaaag ccaaccattg gactgagagc agggccccaa atggaggatt tagagaaaga    6540
acttaaggag ccgaagggac taagacacca accaaagagt acacatggag ggacccatgg    6600
ctcagcctta tatgtaacag aggttggtct tgtcaggcat caatgggagg agaggttctt    6660
ggtcctgtga aggctcgata gatgcccag tgtaggagaa tgccagggtg tgaggtggg    6720 agtgggtggg tgggtgaagg aacaccctca tagaagcagg gggaggggga gtagtataga    6780
gggtttctag aagtgggga aactggaaag ggggataata tttgaaatgt aaataaagga    6840
aatatccaat taaaaaatcc ttacatttaa aaaaagaaa gaaaaccaag gcttaatgat    6900
ggaccaggat ttaatggtac catgacccag tgcagcattg tgagctgcct gacagaggca    6960 tgctcttga taatgggaag agcctagtgg ccagctgtgg gctgtggttg tctctgtttg    7020
ttaacatatt catgatgtca gaggcatgcc tttcctata gtttctgaca agcctgccta    7080
```

```
gtgtgttggt cttccttaac tcatgcaagc gacaacacca ggttagctaa actctacttt    7140
gtgtgatata atatttccta agcaagttca ttagtagatc cttcaagaca tcaatttatc    7200
actctaggat tctcctatgt cacttcatag atttatggtt ttgaattatt aatagaaaaa    7260
taaccccaga tggaactgga aaaaagaaa attcatcttt tttttaaaga tgaaaattat    7320
gctgattctg aattaagaaa aagtaaatat ttataaatat aataaatatt tataataaat    7380
ataatacatg tagaagatat tataatctgt gtattctata tgactaccaa aatttaaagc    7440
tgggaactct tgtagtagcc tattctccag ttgaaaagag atgtcactca tccatcatga    7500
tgggttccgc taggttctca agtagccaaa gcaaacggtt tgtcttctcc cagccttacc    7560
tgattcatct gcagcatggc cacccactga gtggatccca gaagactcaa gagaacttaa    7620
gcaaagtatt gattacattt gagacctcat cactacatct tttcccttgc aaccaaaaca    7680
cacaaacaca cacacacaca aatacacata cgcatacaaa cacacatatg catacaaaca    7740
caaacagaaa catacacaca aacacactca taaccaacac acacacacac actagaagtt    7800
ttagatgttt agttttagac attttagatg gcgattttaa aaataatttc cttcccaaat    7860 ggttgaaaaca aatccagtag ttatctttca ttttatgaaa actaaaatcc aggaagctaa    7920
agctaaaact attcatctaa attttcacta gggaaataaa gactagaatt cctctcaact    7980
tctctgctgc atctgaaact agagtgcaca ctggtcatga ctcccatcac agtaacaggc    8040
cttgcatttt tctgggccag gtggagagtg gcgatgtgtc ccagagcatt taagagcatt    8100
tgatggatga atgacaagat agacaccact aggggggaagt gacagtcggg tatgggacac    8160
aggtggctgc accaattaaa tagacctaag ccagtcacag taatgaggag cctgccttt     8220 ccaattctga ggctttagac ctaaatgcaa ttcgtgcttg tgctgttgtt taactgtctc    8280
agctggaagg ccgagtgtgc ctatttgcaa gccaagggta gttgtaatca tggattttaa    8340
ttaatcgtga ctaaaataca gattagcttt tgttgaagta tttgtcattt gcttcttcta    8400
aacattcagg cataaagtct cacagagatt acattggtct catgctatct tgtcttaaag    8460
tttcgtgtcc actttcctat tgctttaagc caggtatgac ttctacatgc ttctcagccg    8520
acttctgctc ccagtaccgt agttgtgact actgaaagtt agtgaaccaa gaaaggagtt    8580
cacgagcaaa gggcagttgg gttaccttt agtctcctgg agtaaccttg atcacttgtt     8640
tcatttattc aaattgctta tgtgcgtgtg taagatgtta ttgtaaagct tcaaagatg     8700 taagtcgttt ttatttagaa ttcaaagatc atctggtaca gctgatctca acttgagttt    8760
tccccattga ataggaatg aggttccatt tgcagtgatt ccaatttaat tggtagaagc     8820
tgctatcaga ccttgagatt aacgaaagaa atccccagat atgtctaata catagcaaat    8880
cttgagtacc aatgatgtac actttgggca accataacca gaagtggatt tggcaacaaa    8940
tggaatgagg tagccgtgat aaaggacaca gcaaggcaat atgtgcagtg gggagcaccc    9000
cctaacagtc accattcaat ccacttttgt attttctgga aatacaggtg accccaggct    9060
ccacatgtgc cgtgtttggc ctcggagtg tcggtctgtc tgtcatcatt ggctgtaaag     9120
cagcaggagc agccaggatc attgctgtgg acatcaacaa ggacaagttt gccaaggcca    9180
aagagttggg tgcaactgag tgcatcaacc ctcaagacta cagcaaaccc atccaggaag    9240
ttctccagga gatgaccgac ggagggggtgg acttttcgtt tgaagtcatc ggccgccttg    9300
acaccatggt atgtactttg gcacgccttg agatctgtcc ttccatctag aatgctctag    9360
gtagactaac agaaatctca tgcagaaagc tattttttaga gtggtcatct tccatctcct    9420
gtttcctgct cagactgctt aattcgctgt tgagataaac ctttcatttt gtcagttctg    9480
```

```
caaacttgtc tcaagtgcta atcctccttt aatgcaacga agctttcaat ggggacactg    9540
tgaattaact tactgatttt ctgtaaaaaa tcacttcatc gagcaggttt aaatacaaag    9600
tctggtctta aatggatgaa tatgattttc tccctcattc ttaatatttt ttaatattta    9660
gaattgaata ttctgaaaag cattttaag tatcatcata cggccaaaag gaataatgaa     9720
caatttgggg cccaaggatc attttattaa cacacaacac gtagagggaa gtgactgatt    9780
tatacatcac catttagttc tcgttgcaga gacagcacag gctgggcct tccaagcttc     9840
cagatctacc ggttgtagta ataccttttt aaaaaaagaa ttctggcata tctcctaaat    9900
ttaagagata cattttatag gattgcttat gatctccaca agacagtgca tataaaatac    9960
taactgtaga gccctgcca tgtggtaagc actcagtaaa ggtcagctga ggataatgat    10020
aagaaatact acggtcaagc ttagagcgat tggattttgg agtacaaatg acactacagt   10080
caagtagtta caaatgtcat cctttgctaa agaactgttc tccggttaca tctcacctaa   10140
ccaaagacct ctagaactct actgagaaat gtccccaggg agcaaggaag tcaccattat   10200
caaggctctc cacaaagtct tggcagagtt ggtgctggat aataggtatg gcgccctgag   10260
agtgatggtt tggtttagtt ttttttccat ccttgaactg tgacaagatg ccatagactg   10320
tagaagattc aagtgcacag cacctcctct ttccaaaccc aggcttccag ctctccccag   10380
agccactgct ctcgtggctc actggtagat ttctcaatct gctcatctta agctgggctg   10440
tcaattgact tgaagatcca aaagtctgat aaccacatgt tctgaggata tctggtttct   10500
aaacatcata ttgcaaaatc aaaggccact catgtatctt taaggattcc aaatgatttt   10560
ttactagaga atgtgtttta aacaaacaaa caaaaaacca aacaaactaa agaaaagtac   10620
ctattggaag gcaaaaactt cctggatgtc tacagctata gaataatata aaactatcgc   10680
ataaccactt aaaacatgcc cattcttgat gtaagcaccc gaggagggac tcattaaatg   10740
agaatttgac aaatggttaa aagataagtt tgatgatgt catcattta cttcttcacc     10800
attagatttc tggctcagag tactagttta gaaattgtcc ttactgggca aatgaaaagt   10860
gaactaagca gttcatagag agttatgcga tggggaaaca atattctcct ttgagaacca   10920
gactttactt tctcatgatg attcttgcac ctttaaggaa gaattaaaca tagataagtt   10980
aattcattca ctctttcatt aaaaaaagaa aaaatcttc agtgtacttc tttgtaatgc    11040
ctgaaactgc atagtgagga gagaccacaa aagactctac tttaactatt actctttatt   11100
ccagacttct gccctgctga gctgccatgc agcatgtggt gtaagcgtcg tcgtaggagt   11160
gcctcccaat gcccagaacc tctccatgaa ccccatgttg ctgctgctgg gacgcacctg   11220
gaagggagca atatttggcg gtatgtattc acagctcaag atcaatcctg catctgtctg   11280
tatacgtcag ggcgggcgtg tggatgtgtg tgtggaggac agagaacatt cgattcatta   11340
cctgggagcc atttgccacg ttctttgtga cagggtgtca cagtgaccag gctagccttg   11400
ctggctggaa tccactggtt ccctttatcc agagctggaa ttacaagaac tcccacaacc   11460
acatcagctg ttggttggtt ggttggttgg ttggttggtc agttgttgtt tgttattca    11520
aactcaggtt tgactgagcc atctcctcag ctttgaggat caaattttta atgtatttca   11580
gaatttcttc ccttctgtta cagagaaggt cagattttag aaggcaaaac aatttaaaaa   11640
catgaaaatt actgttctct ctaagcaaga actaatgcag gaaattgtaa gacaagcttc   11700
attgtgtccc cataaactag ccagggcttc ttctggctcc tcctacttcc taatgtcatt   11760
gtgagagccc caaaatgcct tataggacac aggaaatcca aggcagtagt agtccatgcc   11820
```

| | |
|---|---|
| tataatcatg acctaagtct gaacagcggt gagaatggca aagctccctt actttgagta | 11880 |
| caaacatctt caatatgatt tctctaggaa agaactaata agccaccttc attagcgaga | 11940 |
| gatcgcggtt tagaggggtg gcatacgata aaaatgttaa tgaaatgcag aatgtttttg | 12000 |
| agcctcagtg tctgtgcagc ctgcagacca ctgttctttt atgaacttta gtttccctgc | 12060 |
| aaagtctggt tggcttgctc cccccgccac tcccccacac attccctccc tccaaccccc | 12120 |
| caggctggat ctcatggaga tgttgctctc cttccagggt ttaagagtaa agattctgtc | 12180 |
| cctaaacttg tggctgactt catggctaag aagtttccgt tggacccgtt aattacccat | 12240 |
| gttttacctt tcgagaaaat aaatgaagca tttgacctgc ttcgttctgg aaagaggtaa | 12300 |
| gctttgagat tatttttatg gcagaggaat tggctaacag aaaatgaagg agaagtggga | 12360 |
| taagaccata aatgaagggg gtgggggaag gggctggctt ctgtcaccag tttggctctg | 12420 |
| cacacaggta tatgacatag gacaattgca aacctaagct ttagtttcca cagttcctaa | 12480 |
| aggtgacaat atgtgataat ccaccttgta gtattgctgt ttaggatgag gtttaaatga | 12540 |
| gataaccatg ccttaaaagc ttccataaag cacatggcag gtagcaagga ggaaatggct | 12600 |
| ggtgttgccc attgttacac aagggatcca gacttttagt gttgtttaag agtgctaaac | 12660 |
| tagaaccgga atcaaaatgg cagtcacatc aggatgttaa gtgtgagttt agagctggag | 12720 |
| agaatgcaag agcgatcaga aaggtggatt gctcgtttac tgacttgacc ttgggcatag | 12780 |
| catggttggg aacccggata gattttctca gagactccta acatgtcttc tactcacttt | 12840 |
| tatggtgagt tatggaatgt gaaatcacta tcttctgttc tgtatttcag catccgtacc | 12900 |
| gtcctgactt tctgagatca tgtggatgcc ttcccacgca ccagtttctg aaccctaaac | 12960 |
| cagactgatt caagcaccag ccacatcaca gccttaatct ttgctcttta gagacacagc | 13020 |
| caataaagta cttgtgtaag ctctcca | 13047 |

<210> SEQ ID NO 29
<211> LENGTH: 2024
<212> TYPE: DNA
<213> ORGANISM: Arabidopsis thaliana

<400> SEQUENCE: 29

| | |
|---|---|
| tctacttctt ccaattacca gctgctatat aaatccccTT ctctgtttct cttttcttac | 60 |
| atcacaatca cacaaaacta acaaaagatc aaaagcaagt tcttcactgt tgataatgtc | 120 |
| taccaccgga cagattattc gatgcaaagg ttttctttTT attctgtctt tttccaaata | 180 |
| tttattgatc ggttacattt ctgttgaggt ttttgttatg aatccacaat ttctatgttg | 240 |
| aattaacaaa acctgtgtcg ttttTTTgtg gtggttgcag ctgctgtggc atgggaagcc | 300 |
| ggaaagccac tggtgatcga ggaagtggag gttgctccac cgcagaaaca cgaagttcgt | 360 |
| atcaagattc tcttcacttc tctctgtcac accgatgttt acttctggga agctaaggta | 420 |
| gagtaatcaa tttattacac tccaaattca taatcaagtt ctaattTTTT tagaattcta | 480 |
| atttTTTatc taaaaaaatt caaccttTTT gattccacag ggacaaacac cgttgtttcc | 540 |
| acgtatcttc ggccatgaag ctggagggta atagaaacac taatcttctt tgcttcgttt | 600 |
| tggatatttt taaggtttta gagattcaag gtcgttTTTT ttgttgttgt gtaggattgt | 660 |
| tgagagtgtt ggagaaggag tgactgatct tcagccagga gatcatgtgt tgccgatctt | 720 |
| taccggagaa tgtggggagt gtcgtcattg ccactcggag gaatcaaaca tgtgtgatct | 780 |
| tctcaggatc aacaccgagc gaggagggat gattcacgat ggtgaatcaa gattctccat | 840 |
| taatggcaaa ccaatttacc atttccttgg gacttccacg ttcagtgagt acacagtggt | 900 |

| | | | | |
|---|---|---|---|---|
| tcactctggt | caggttgcta | agatcaatcc | ggatgctcct | cttgacaagg tctgtattgt | 960 |
| cagtgtggt | ttgtctactg | ggttaggagc | aactttgaat | gtggctaaac ccaagaaagg | 1020 |
| tcaaagtgtt | gccattttg | gtcttggtgc | tgttggttta | ggcgctgcag aaggtgctag | 1080 |
| aatcgctgg | gcttctagga | tcatcggtgt | tgattttaac | tctaaaagat tcgaccaagg | 1140 |
| tattcaaaaa | gatgatagtc | tgttttgac | tatgttcttc | tataatctcc cttcacttac | 1200 |
| attgaatttg | atatgttatt | ggcagctaag | gaattcggtg | tgaccgagtg tgtgaacccg | 1260 |
| aaagaccatg | acaagccaat | tcaacaggtg | atcgctgaga | tgacggatgg tggggtggac | 1320 |
| aggagtgtgg | aatgcaccgg | aagcgttcag | gccatgattc | aagcatttga atgtgtccac | 1380 |
| gatgtaatcc | tcccttcaca | tcattcggac | caaaacttt | gtaactacat tgtgggtatc | 1440 |
| tgaacttatc | acatatgatg | ttgtttcagg | gctggggtgt | tgcagtgctg gtgggtgtgc | 1500 |
| caagcaaaga | cgatgccttc | aagactcatc | cgatgaattt | cttgaatgag aggactctta | 1560 |
| agggtacttt | cttcgggaac | tacaaaccca | aaactgacat | tcccggggtt gtggaaaagt | 1620 |
| acatgaacaa | ggtaatgaga | agctttgata | tcttatgatg | ccaactttga atatatatca | 1680 |
| atgttctgat | gattttatg | acataggagc | tggagcttga | gaaattcatc actcacacag | 1740 |
| tgccattctc | ggaaatcaac | aaggcctttg | attacatgct | gaagggagag agtattcgtt | 1800 |
| gcatcatcac | catgggtgct | tgaagccatt | ctctcgcaga | tgatgttcac tttgtgtttt | 1860 |
| acttccttta | tgcattcaca | gcaataaaag | aaagaaatct | ccatcgcttt tggttttctt | 1920 |
| ctctgtctta | agttagtcgt | tttcgtgtct | aatctattac | ttatcattgt aatagactct | 1980 |
| tcttctattg | agatttgaat | ataaactaaa | acacattcca | tttt | 2024 |

<210> SEQ ID NO 30
<211> LENGTH: 2655
<212> TYPE: DNA
<213> ORGANISM: Saccharomyces cerevisiae

<400> SEQUENCE: 30

| | | | | |
|---|---|---|---|---|
| atggatccta | atagtaacag | ttctagcgaa | acattacgcc | aagagaaaca gggtttccta | 60 |
| gacaaagctc | ttcagagggt | gaagggcata | gcactgcgac | gaaacaatag taacaaagat | 120 |
| catacaacag | atgatacgac | aggtagcata | cgaacccta | cgagcttgca gcggcaaaat | 180 |
| tctgacaggc | aatctaatat | gacatccgtg | tttacggatg | acatttctac catagacgac | 240 |
| aactcaattt | tattttcaga | gcctcctcag | aaacaatcta | tgatgatgtc tatatgcgta | 300 |
| ggtgttttg | ttgcagttgg | cggatttta | tttggttatg | atacaggtct gatcaacagt | 360 |
| attacatcta | tgaactatgt | gaagtcacac | gtagcaccta | tcacgattc atttaccgcc | 420 |
| caacaaatgt | ccattttggt | gtcattttg | tcattgggaa | cttttttgg ggctttaact | 480 |
| gcaccattta | tatctgattc | gtatggcagg | aagcctacta | tcattttcag tacaattttc | 540 |
| atcttctcta | tcggaaattc | tttacaggta | ggtgctggag | gaatcacatt attgattgtg | 600 |
| ggaagggtca | tttcaggtat | cggtataggc | gcaatttcag | cggttgttcc attataccaa | 660 |
| gcagaagcta | cacataaatc | attaagaggt | gctattattt | ctacttacca atgggccatt | 720 |
| acctggggct | tgctcgtgtc | aagtgcagtg | tcgcaaggga | cacacgcaag aaacgacgca | 780 |
| tcttcgtatc | ggattcccat | agggttgcaa | tatgtctggt | cgtcatttct cgctatcggg | 840 |
| atgttctttc | tccctgagag | tccacgctat | tacgttttga | aagacaagct agatgaagca | 900 |
| gctaaatctt | tatcgttttt | aagaggtgta | ccagtccatg | attctgggtt actggaagaa | 960 |

```
ctagttgaaa taaaggcaac atatgattac gaggcatctt ttggttcttc gaacttcatt    1020
gattgtttta tttcaagtaa aagtagacca aagcaaactc taaggatgtt tacgggaatt    1080
gcccttcaag catttcaaca attttcaggt atcaacttta tattttacta cggtgtcaat    1140
ttcttcaata agacaggagt cagtaatagt tatctggttt catttataac ctatgctgtt    1200
aatgttgtct ttaatgttcc tggtttgttt tttgtggaat ttttggtag acgtaaggtg     1260 ctggttgttg ggggtgttat catgactata gccaacttta ttgtggccat tgttgggtgt    1320
tccttaaaga ctgtagcggc cgcaaaagtt atgatagcat ttatatgtct attcatagct    1380
gccttttctg ctacatgggg tggtgttgtt tgggttattt cagcagaact gtacccattg    1440
ggtgtgagat ctaaatgtac ggctatatgc gctgctgcta actggcttgt aaactttatt    1500
tgtgctttaa ttaccccta tattgtagat actgggtcgc atacatcatc attaggtgca    1560
aaaatattct tcatttgggg ctccttaaat gcgatggggg tgatagttgt ttacttgacc    1620
gtttatgaaa cgaagggttt gacattagaa gagattgatg aattatatat taagtcatcc    1680
actggtgtcg tgtcaccaaa atttaataaa gatattaggg aacgcgcact taaattccaa    1740
tacgatcctt tgcaaagatt agaagacgga agaacacttt tgttgctaa aagaaataat     1800 tttgacgatg aaacaccaag aaatgatttt cgaaatacga tatcgggcga aatagatcat    1860
agtcccaatc aaaagaagt tcattctatc ccagaacgtg ttgatattcc tactagtaca     1920
gaaattcttg aaagcccgaa caaaagtagt ggtatgacag tccctgtgtc accttctctg    1980
caagacgttc caatcccgca acaacagag cctgctgaaa ttcgaaccaa atatgtggac     2040
ctaggaaatg ggcttggtct taatacgtat aatagagggc ctccctcact ctcaagcgac    2100
tcaagcgaag attacacaga agatgaaata ggcgggccct catctcaagg cgaccaaagt    2160
aatagaagta ctatgaatga tattaatgat tatatgcac gtctcattca cagtacttct      2220
actgcaagta acacgacaga taagttctcc ggtaaccaaa gtaccttcg ttaccacacg      2280 gcttcctcac attcggatac aactgaagag gacagcaatt tgatggacct gggaaacggg    2340
cttgccttga atgcttataa cagaggtcca ccttcaattt taatgaattc cagtgatgaa    2400
gaggcaaatg gtggtgagac gtctgataat ttgaacacag ctcaagactt ggctggtatg    2460
aaggaacgaa tggcgcagtt tgcgcagagc tatattgaca agagaggcgg tctggaacct    2520
gaaactcaat ctaatatttt gagcacttct ctctccgtga tggctgacac taatgaacat    2580
aataatgaaa tcctccactc aagcgaagaa aacgccacta atcaacctgt aaatgaaaat    2640
aatgatttga aataa                                                     2655

<210> SEQ ID NO 31
<211> LENGTH: 2655
<212> TYPE: DNA
<213> ORGANISM: Saccharomyces cerevisiae

<400> SEQUENCE: 31
atggatccta atagtaacag ttctagcgaa acattacgcc aagagaaaca gggtttccta     60
gacaaagctc ttcagagggt gaagggcata gcactgcgac gaaacaatag taacaaagat    120
catacaacag atgatacgac aggtagcata cgaaccccta cgagcttgca gcggcaaaat    180
tctgacaggc aatctaatat gacatccgtg tttacggatg acatttctac catagacgac    240
aactcaattt tattttcaga gcctcctcag aaacaatcta tgatgatgtc tatatgcgta    300
ggtgtttttg ttgcagttgg cggattttta tttggttatg atacaggtct gatcaacagt    360
attacatcta tgaactatgt gaagtcacac gtagcaccta atcacgattc atttaccgcc    420
```

```
caacaaatgt ccattttggt gtcatttttg tcattgggaa ctttttttgg ggctttaact      480
gcaccattta tatctgattc gtatggcagg aagcctacta tcattttcag tacaattttc      540
atcttctcta tcggaaattc tttacaggta ggtgctggag gaatcacatt attgattgtg      600
ggaagggtca tttcaggtat cggtataggc gcaatttcag cggttgttcc attataccaa      660
gcagaagcta cacataaatc attaagaggt gctattattt ctacttacca atgggccatt      720
acctggggct tgctcgtgtc aagtgcagtg tcgcaaggga cacacgcaag aaacgacgca      780
tcttcgtatc ggattcccat agggttgcaa tatgtctggt cgtcatttct cgctatcggg      840
atgttctttc tccctgagag tccacgctat tacgttttga agacaagct agatgaagca       900 gctaaatctt tatcgttttt aagaggtgta ccagtccatg attctgggtt actggaagaa      960
ctagttgaaa taaaggcaac atatgattac gaggcatctt ttggttcttc gaacttcatt     1020
gattgtttta tttcaagtaa aagtagacca aagcaaactc taaggatgtt tacgggaatt     1080
gcccttcaag catttcaaca attttcaggt atcaacttta tattttacta cggtgtcaat     1140
ttcttcaata agacaggagt cagtaatagt tatctggttt catttataac ctatgctgtt     1200
aatgttgtct ttaatgttcc tggtttgttt tttgtggaat tttttggtag acgtaaggtg     1260
ctggttgttg ggggtgttat catgactata gccaacttta ttgtggccat tgttgggtgt     1320 tcctaaaga ctgtagcggc cgcaaaagtt atgatagcat ttatatgtct attcatagct      1380
gccttttctg ctacatgggg tggtgttgtt tgggttattt cagcagaact gtacccattg     1440
ggtgtgagat ctaaatgtac ggctatatgc gctgctgcta actggcttgt aaactttatt     1500
tgtgctttaa ttaccccta tattgtagat actgggtcgc atacatcatc attaggtgca     1560
aaaatattct tcatttgggg ctccttaaat gcgatggggg tgatagttgt ttacttgacc     1620
gtttatgaaa cgaagggttt gacattagaa gagattgatg aattatatat taagtcatcc     1680
actggtgtcg tgtcaccaaa atttaataaa gatattaggg aacgcgcact taaattccaa     1740
tacgatcctt tgcaaagatt agaagacgga aagaacactt tgttgctaa aagaaataat      1800 tttgacgatg aaacaccaag aaatgatttt cgaaatacga tatcgggcga aatagatcat     1860
agtcccaatc aaaaagaagt tcattctatc ccagaacgtg ttgatattcc tactagtaca     1920
gaaattcttg aaagcccgaa caaaagtagt ggtatgacag tccctgtgtc accttctctg     1980
caagacgttc aatcccgca aacaacagag cctgctgaaa ttcgaaccaa atatgtggac      2040
ctaggaaatg ggcttggtct taatacgtat aatagagggc ctccctcact ctcaagcgac     2100
tcaagcgaag attacacaga agatgaaata ggcgggccct catctcaagg cgaccaaagt     2160
aatagaagta ctatgaatga tattaatgat tatatggcac gtctcattca cagtacttct     2220
actgcaagta acacgacaga taagttctcc ggtaaccaaa gtaccttcg ttaccacacg      2280 gcttcctcac attcggatac aactgaagag gacagcaatt tgatggacct gggaaacggg     2340
cttgccttga tgcttataaa cagaggtcca ccttcaattt taatgaattc cagtgatgaa     2400
gaggcaaatg gtggtgagac gtctgataat ttgaacacag ctcaagactt ggctggtatg     2460
aaggaacgaa tggcgcagtt tgcgcagagc tatattgaca agagaggcgg tctggaacct     2520
gaaactcaat ctaatatttt gagcacttct ctctccgtga tggctgacac taatgaacat     2580
aataatgaaa tcctccactc aagcgaagaa aacgccacta tcaacctgt aaatgaaaat      2640 aatgatttga ataa                                                      2655
```

<210> SEQ ID NO 32

<211> LENGTH: 1581
<212> TYPE: DNA
<213> ORGANISM: Candida albicans

<400> SEQUENCE: 32

```
atgagtgcaa atatccaagc tcttatgaaa agctatgtca attttgacga acacacttct      60
ggttccgctg ccagaggtat tttaatcggt atgtttgctg cttttggtgg gttttgttt     120
ggttacgaca ctggtactat ttctggtgta ttgtctatgg actacgttaa agccagattc     180
cccaacaaca aaccgatttt cacttctggt gaaagttccc ttattgtctc cattttatca    240
gtcggtactt ttgttggttc cttgattgcc ccattgtttt ccgatagaat tggtcgtaga    300
tggacattga ttttatctac tttgattgtt tttaacttgg gagttctttt acaaactgtt    360
gccactgaaa agaaattgct tattgcaggt agagccattg ccggtactgg tgttggttta    420
atttcatctg ttattcctaa ttatatttcg gaaacaacac caaagtgggc tagaggtgct    480
gtcactgctt cataccaatg gatgatcacc tggggtcttt taattgctgc ttgtgccaac    540
aagggttccc aaggtagaaa agactctggt tcctatagaa tacccattgg tattcaattt    600
ttgtgggcat tgattttggg tattggtttc ttgtttctcc cagaaacccc aagatactgg    660
gtttccaagt ctgaagaaac taaagctaaa gattctttga agaattag aaacttgcct     720
gttgatcacc cagatttggt gctggaatac gatgacatta agcaaactt tgatttcgaa     780
tccaaatatg ccacttcttc ttggacccaa gttttcaaaa cgttaacaa acaacaccac     840
agattattca ctggggttgc catccaagct ttgcaacaac ttactggtat taatttcatc    900
ttctactatg gtactcaatt cttcaagcgt tctggtattg aagatccttt ccttatccaa    960
cttgccacta atattgttaa tgttggtatg actgtgccgg gtattatttt ggttgaaacc   1020
tggggtagaa gaccattgtt gatggccggt agtgttgtta tggctgtctc ccaattgatt   1080
gttgccattg ttggtgttgc tgctagcagt catgctgcaa atcaatgttt agttgctttc   1140
agttgtattt tcattgctgg tttcgcagca acttggggac ctctttgttg ggctatttgt   1200
ggtgaatcct ttgctttgaa cgtgagactg aaatcaatct ccttgtgtac cgcaagtaac   1260
tggctttgga atttcggtat tggttatgct actccttata tggttgattc aggtaaaggg   1320
aacgccgact tgggttcaaa ggtgttttc atttggggtg gatgtaacgt cattggtggg    1380
ttgtttgcat actttatggt ttacgaaacc aagagtctta cattagaaca agttgatgaa   1440
ttgtacttga agttgatca cgcttggcaa tctaaaggat ttgttcctag tgtccacgca    1500
tttagagatg atggcgatat tgagcacatc tcttctgatg gaaaagccga aatggttgaa   1560
gttgatgaaa attccgttta a                                             1581
```

<210> SEQ ID NO 33
<211> LENGTH: 111
<212> TYPE: DNA
<213> ORGANISM: Ostreococcus tauri

<400> SEQUENCE: 33

```
cgcgcgtcgt gcgagtggct cgatcgatct cacgctcgat cgcgtctgag aacacatcgc    60
tggaacttga ctcaggataa tacctgcgta aggaacgacc gcggcatcgc g            111
```

<210> SEQ ID NO 34
<211> LENGTH: 1362
<212> TYPE: DNA
<213> ORGANISM: Artificial sequence
<220> FEATURE:
<223> OTHER INFORMATION: Synthetic construct -continued

```
<400> SEQUENCE: 34
tggctgcgtc tggtgggacc gttgtatacg ccggtagtgg tttgcggggc tacggcgagt      60
tggtcatcat caaacacaac gagacctacg tgagtgccta cggtcacaac cgcaggctgc     120
tggtgcggga agggcaacag gtcaaggtag ggcaatcgat tgccgagatg ggctccacag     180
gaaccgatcg ggtgaagctg cacttcgaga ttcgccgcca gggtaagcct gtcgatccac     240
tgcaatattt gccacgtcgc tgaccggagt tcgcccgcc cacatcatgt aggtgagcgg      300
gtccgggcgt gtccagcggg aaaggaatcg cccgggcttg agtcgaactc atgcaaggga    360
taacgacatg gcactcaaaa aagaagggcc ggagtttgac cacgatgatg aagtgctcct    420
cctggagccc ggcatcatgc tggacgagtc gtctgccgac gagcagcctt ctccccgggc    480
aactccaaaa gccaccactt ccttctcttc caaacaacac aagcacatcg actacacgcg    540
cgcgttggac gcaacgcagc tgtatctcaa cgaaatcggt ttctcgcccc tgttgacgcc    600
cgaagaggaa gtccacttcg ctcgtctggc gcagaagggc gatcccgctg gtcggaagcg    660
gatgatcgag agcaacctgc ggttggtggt gaagatcgcc cggcgctatg tcaatcgcgg    720
actgtccctg ctcgacctga tcgaggaagg caacctaggc ctgatccgcg ccgtggagaa    780
gttcgatccg gagcgcggat tccggttctc gacctacgcc acctggtgga tccgccagac    840
catcgagcgg gccatcatga accagacccg gaccattcgc ttgccgatcc atgtggtcaa    900
ggagctcaac gtctacctgc gtgcggcgcg ggaactgacc cacaagctcg accacgaacc    960
ttcacccgaa gaaatcgcca acctgctgga gaagccggtc gccgaggtca gcgcatgct    1020 cggcctgaac gaacgggtga cttcggtaga cgtctctctt ggtccggact cggacaagac   1080
cctgctggat acgctcaccg acgatcgccc caccgatccg tgcgagctgc tgcaggatga   1140
cgatctcagc gaaagcagct gacggaactc accgacaagc agcgtgaggt ggtgattcgc   1200
cgcttcggct tgcgcggtca cgaaagcagc acgctggaag aggtcggcca ggaaatcggc   1260
ctgacccgcg agcgggttcg tcagatccag gtcgaggcgc tgaagcgcct gcgggagatt   1320
ctggagaaga atggcctgtc gagtgacgcg ctgttccagt ga                      1362

<210> SEQ ID NO 35
<211> LENGTH: 18
<212> TYPE: DNA
<213> ORGANISM: Artificial sequence
<220> FEATURE:
<223> OTHER INFORMATION: Synthetic construct

<400> SEQUENCE: 35
cccgccgcca ccatggag                                                    18

<210> SEQ ID NO 36
<211> LENGTH: 13
<212> TYPE: DNA
<213> ORGANISM: Artificial sequence
<220> FEATURE:
<223> OTHER INFORMATION: Synthetic construct

<400> SEQUENCE: 36
tcacacagga aag                                                         13
```